(12) United States Patent
Zwirn

(10) Patent No.: US 8,784,320 B2
(45) Date of Patent: *Jul. 22, 2014

(54) ULTRASOUND GARMENT

(71) Applicant: Volusonics Medical Imaging Ltd., Petach-Tikva (IL)

(72) Inventor: Gil Zwirn, Petach-Tikva (IL)

(73) Assignee: Volusonics Medical Imaging Ltd, Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/682,155

(22) Filed: Nov. 20, 2012

(65) Prior Publication Data
US 2013/0079641 A1    Mar. 28, 2013

Related U.S. Application Data

(63) Continuation of application No. 12/994,221, filed as application No. PCT/IL2009/000522 on May 26, 2009, now Pat. No. 8,465,433.

(60) Provisional application No. 61/056,069, filed on May 27, 2008.

(51) Int. Cl.
*A61B 8/14* (2006.01)

(52) U.S. Cl.
USPC .......................................... 600/459; 600/437

(58) Field of Classification Search
USPC ................................................ 600/437–469
See application file for complete search history.

(56) References Cited

U.S. PATENT DOCUMENTS

| 7,597,665 | B2 * | 10/2009 | Wilk et al. | ..................... 600/459 |
| 7,634,318 | B2 * | 12/2009 | Tran et al. | ........................ 607/61 |
| 2006/0100530 | A1 * | 5/2006 | Kliot et al. | ..................... 600/483 |
| 2011/0319760 | A1 * | 12/2011 | Cerofolini | ..................... 600/443 |

* cited by examiner

*Primary Examiner* — Sanjay Cattungal
(74) *Attorney, Agent, or Firm* — Symbus Law Group, LLC; Clifford D. Hyra

(57) ABSTRACT

Disclosed is an ultrasound assembly. The ultrasound assembly includes a garment configured to be affixed to a portion of a living body, and at least one ultrasound transducer having a fixed position on the garment and configured to provide at least one of: produce and receive, ultrasound signals that pass through the living body. The ultrasound assembly further includes an ultrasound processing unit operatively associated with the at least one ultrasound transducer and configured to process the ultrasound signals following passage through the living body, and an ultrasound-interface unit operatively associated with the ultrasound processing unit and configured to provide information with respect to the ultrasound signals following passage through the living body.

19 Claims, 8 Drawing Sheets

ULTRASOUND GARMENT

RELATED APPLICATION

This application claims priority from U.S. Patent Application Ser. No. 61/056,069 filed 27 May 2008, the content of which is hereby incorporated by reference as if fully set forth herein.

FIELD AND BACKGROUND OF THE INVENTION

The present invention, in some embodiments thereof, relates to fixing the position of an ultrasound transducer with respect to a subject and, more particularly, but not exclusively, to fixing the position of an ultrasound transducer within a garment affixed to the subject.

Ultrasound is a well matured medical imaging modality. It provides two-dimensional (2D) and/or three-dimensional (3D) anatomic information as well as a plurality of physiological and functional parameters at relatively high refresh rates, reaching an order of 100 frames per second for 2D imaging.

The imaging platforms are portable and reasonably priced. However, ultrasound imaging suffers from some disadvantages, chief of which are low image quality compared to other imaging modalities, for example Computed Tomography (CT) and Magnetic Resonance Imaging (MRI); and limited volume coverage.

Conventional phased array transducers have a limited field of view due to limitations at the beam steering end, i.e., due to off-broadside beam widening; the effective area of planar transducers decreases with the off-broadside angle, thus increasing the beam width.

The maximal beam penetration depth is also limited by signal attenuation within the tissue. Decreasing the transmission frequency reduces the attenuation and increases the penetration depth, but also worsens the spatial resolution.

One of the methods known in the art for addressing these issues is image registration and compounding. The term 'registration' relates to the process of finding a transformation that maps each point in one image or coordinate system to corresponding points in another image or coordinate system. The term 'compounding' relates to the combination of data from multiple registered images to produce one or more registered images.

The registration process may either be algorithm based, or sensor based.

In algorithm based registration, the sole input is a set of reconstructed imaging planes or volumes. For example as described by Foroughi P, Abolmaesumi P, Hashtrudi-Zaad K; "Intra-Subject Elastic Registration of 3D Ultrasound Images"; Medical Image Analysis 2006; 10:713-725.

In sensor based registration, data acquired by positioning and/or orientating sensors is also utilized. For example as taught in US Patent Application 2007/0081709; Apr. 12, 2007 by Warmath R J, Herline A J; "Method and Apparatus for Standardizing Ultrasonography Training Using Image to Physical Space Registration of Tomographic Volumes from Tracked Ultrasound".

The documented advantages and features of ultrasound image registration and compounding include, for instance:

i. Field of view extension; for example as described by Poon T C, Rohling R N; "Three-Dimensional Extended Field-Of-View Ultrasound"; Ultrasound in Medicine and Biology 2006; 32:357-369.

ii. Freehand three-dimensional (3D) imaging, i.e., generation of 3D images using a manually moved 2D imaging probe; for example as described by Treece G M, Gee A H, Prager R W; "RF and Amplitude-Based Probe Pressure Correction for 3D Ultrasound"; Ultrasound in Medicine and Biology 2005; 31:493-503.

iii. Speckle noise reduction. Speckle is a result of the fact that the reflecting particles within tissues are much smaller than the wavelength used. The effect of speckle may be modeled as multiplicative noise. Speckle patterns are very sensitive to small changes in the relative location of the transducer and the tissue volume, and can be reduced by local averaging over several frames, taken at different times or probe positions/orientations. For example as described by Krücker J F, Meyer C R, LeCarpentier G L, Fowlkes J B, Carson P L; "3D Spatial Compounding of Ultrasound Images Using Image-Based Nonrigid Registration"; Ultrasound in Medicine and Biology 2000; 26:1475-1488.

iv. Minimization of shadowing artifacts. Shadowing is caused by tissues along the ultrasonic beam that have a high reflection and/or attenuation coefficient, so that the ultrasound energy reaching tissues further away from the transducer (along the ultrasonic beam) is significantly reduced. This differently affects ultrasound images acquired from different angles, and can therefore be mitigated by spatial compounding. For example, as described by Krücker J F, Meyer C R, LeCarpentier G L, Fowlkes J B, Carson P L; "3D Spatial Compounding Of Ultrasound Images Using Image-Based Nonrigid Registration"; Ultrasound in Medicine and Biology 2000; 26:1475-1488.

v. Spatial resolution enhancement, using datasets obtained at multiple spatial locations and/or orientations of the probe; for example as described by Yang Z, Tuthill T A, Raunig D L, Fox M D, Analoui M; "Pixel Compounding: Resolution-Enhanced Ultrasound Imaging for Quantitative Analysis"; Ultrasound in Medicine and Biology 2007; 33:1309-1319.

vi. Estimation of speed of sound factors within different tissues, using time delays measured at different directions; for example as taught in US Patent Application 2007/0167757; Jul. 19, 2007; Haimerl M; "Determining Speed-of-Sound Factors in Ultrasound Images of a Body".

vii. Change estimation and regional motion evaluation, utilizing 2D or 3D imaging information acquired for the same tissue volume at several timeframes. In some cases, the registration may be performed globally, but local registration is usually required, tracking the location change over time for every small region, for example as described by optic-flow techniques. If the time difference between consecutive images is relatively short, applying cross-correlation functions to the local speckle pattern can allow accurate regional motion assessment. For example as taught in U.S. Pat. No. 5,876,342; Mar. 2, 1999; Chen J F, Weng L; "System and Method for 3-D Ultrasound Imaging and Motion Estimation".

viii. Angle independent Doppler measurement. Standard ultrasound systems estimate flow velocity, for example blood flow velocity, using the Doppler Effect, which only provides information regarding the radial component of the velocity vector. When multiple receiving transducers are employed, placed at different angular locations with respect to the target volume, one can estimate the magnitude and orientation of the flow velocity vector. For example as taught in U.S. Pat. No. 5,409,010; Apr. 25, 1995; Beach K, Overbeck J; "Vector Doppler Medical Devices For Blood Velocity Studies".

ix. Intra-operative guidance, by registration of intra-operative ultrasound images to images acquired beforehand by any modality; for example as described by Barratt D C, Penney G P, Chan C S K et al.; "Self-Calibrating 3D-Ultrasound-Based Bone Registration for Minimally Invasive Orthopedic Surgery"; IEEE Transactions on Medical Imaging 2006; 25:312-323.

Some state-of-the-art 3D imaging probes with improved field of view have also been suggested, for instance:

i. As taught in International Patent Application WO2004/001447; Dec. 31, 2003; Poland and Sumanaweera et al.; "System and Method for Electronically Altering Ultrasound Scan Line Origin for a Three-Dimensional Ultrasound System"; and as taught in US Patent Application 2006/0078196; Apr. 13, 2006; Sumanaweera T S, Cai A H, Ustuner K F; "Distributed Apexes for 3-D Ultrasound Scan Geometry"; which describe 2D or multi-dimensional (MD) phased arrays which can adaptively generate scan lines apparently emanating from a location ("apex") other than the geometric center of the transducer probe. Multiple apexes may be generated, allowing the optimization of the scanned volume to the transducer's characteristics.

ii. As taught in US Patent Application 2006/0173333; Aug. 3, 2006; Sudol W.; "Two-Dimensional Transducer Arrays for Improved Field of View"; where a similar concept is presented, wherein different groups of adjacent rows and/or columns of transmitting and/or receiving transducer components are activated at different times. Sudol also suggests the possibility of using a convex 2D array, as well as using two or more probes concurrently.

iii. As taught in US Patent Application 2007/0066902; Mar. 22, 2007; Wilser and Mohr; "Expandable Ultrasound Transducer Array"; describing a foldable transducer array, intended to be used within the subject's body. While folded, the transducer array has a smaller width or volume, for insertion into and withdrawal from, for example a hollow region within the subject. When unfolded, foldable transducer array provides a larger radiation surface.

Another system and technique, which effectively improves image quality and increases image volume, is ultrasound computed tomography (UCT). UCT is founded on inverse problem concepts, similar to those used for X-ray CT. UCT has two basic implementations:

i. Reflection mode: In this case, the source, for example the transmitting array, and the detector, for example the receiving array; are on the same side of the subject or the target region. The transmitting array and the detector are rotated about a certain rotation axis, and in some cases also translated along that axis. In each geometric configuration, a short ultrasound pulse is transmitted, and the reflected echoes, resulting from discontinuities in the speed of sound within the medium, are measured as a function of time, which corresponds to the distance between the reflector and the transducer; for example as taught in US Patent Application 2006/0106307; May 18, 2006; Dione D P, Staib L H, Smith W; "Three-Dimensional Ultrasound Computed Tomography Imaging System".

ii. Transmission mode: In this configuration, the source and the detector are placed on opposite sides of the subject or the target region, and are rotated and/or translated together; for example as taught in U.S. Pat. No. 4,509,368; Apr. 9, 1985; Whiting J F, Koch R H L; "Ultrasound Tomography". For each beam, the time difference between the transmission of the pulse and its detection on the other side; for example as described by using rise-time detection or threshold detection on receive; provides information regarding the overall time of flight, which is inversely proportional to the average speed of sound along the beam. The power ratio between the transmitted pulse and the received pulse provides an estimate of the total signal attenuation along the beam.

In some cases, multiple sources and/or detectors are used to reduce the overall scanning time.

Both UCT modes use circular or helical scanning of the subject. A slightly different geometry has been suggested by Li P C, Huang S W; "Ultrasound Tomography of the Breast Using Linear Arrays"; ICASSP 2005; V-989-V-992; who compressed a female breast between a linear transducer array and a reflective metal plate. Separate groups of transducer components are allocated for signal transmission and reception. The relative location of the selected groups with respect to the metal plate determines the path of the ultrasonic beam.

A variation of UCT, called ultrasound diffraction tomography (UDT), is based on measuring the forward scattered ultrasound field as a function of cross-range with respect to the incident wave. This technique also requires the utilization of more complex reconstruction methods; for example as described by Louis A K; "Medical Imaging: State of the Art and Future Development"; Inverse Problems 1992; 8:709-738.

Furthermore, ultrasound imaging has the potential to expand its clinical applications beyond its presently prevalent capabilities, and also provide tissue classification parameters. Elastography has been proposed as a way to achieve this goal; for example as described by Melodelima D, Bamber J C, Duck F A, Shipley J A, Xu L; "Elastography for Breast Cancer Diagnosis using Radiation Force: System Development and Performance Evaluation"; Ultrasound in Medicine and Biology 2006; 32:387-396. The term elastography encompasses a variety of techniques that can depict a mechanical response or property of tissues. In ultrasound, the elastography premise is built on two known facts:

i. There are significant differences between mechanical properties of several tissue components.

ii. The time-dependent information contained in the measured speckle patterns is sufficient to depict these differences following an external or internal mechanical stimulus. This stimulus may be generated, for example by applying an external pressure to the skin surface, or by vibrating a region at a low frequency.

Ultrasound also has therapeutic applications, using high intensity focused ultrasound (HIFU) technologies, which increase the local temperature at a region near the focal point of a high energy ultrasound transducer, thus causing local tissue ablation; for example as taught in US Patent Application 2008/0051656; Feb. 28, 2008; Vaezy S, Chan A N, Fujimoto V Y, Moore D E, Martin R W; "Method for Using High Intensity Focused Ultrasound".

SUMMARY OF THE INVENTION

According to an aspect of some embodiments of the invention, there is provided an ultrasound assembly. The ultrasound assembly includes a garment configured to be affixed to a portion of a living body, and at least one ultrasound transducer having a fixed position on the garment and configured to provide at least one of: produce and receive ultrasound signals that pass through the living body. The ultrasound assembly further includes an ultrasound processing unit operatively associated with the at least one ultrasound transducer and configured to process the ultrasound signals following passage through the living body, and an ultrasound operator-interface unit operatively associated with the ultrasound processing unit and configured to provide information with respect to the ultrasound signals following passage through the living body.

In some embodiments of the invention, the garment is configured to cover at least a portion of a body part of the living body including at least one of: an abdomen, a torso, a pelvis, an arm, a foot, and a head.

In some embodiments of the invention, the garment comprises at least one apparel including at least one of: a belt, a shirt, and a pair of pants.

In some embodiments of the invention, the garment is comprised of at least two parts, separated by at least one band, the at least one band being at least one of: relatively stretchable, and relatively unstretchable.

In some embodiments of the invention, the garment has an open configuration which may be adjustably closed around at least a portion of a body part and includes a closure including at least one of: Velcro, straps, tape, and clips.

In some embodiments of the invention, the garment includes an inner surface and an outer surface and includes, to keep the garment in place, at least one of: sticky patches on the inner surface, vacuum chambers on the inner surface, and pressure chambers on the outer surface.

In some embodiments of the invention, the garment includes at least one fixation point to which the at least one transducer removably attaches.

In some embodiments of the invention, the garment is configured to receive at least one mechanical fixture operatively associated with the at least one transducer, the mechanical fixture configured to maintain the at least one transducer affixed to the garment.

In some embodiments of the invention, the at least one transducer comprises at least one transducer array.

In some embodiments of the invention, the at least one transducer array comprises a plurality of transducer arrays.

In some embodiments of the invention, the plurality of transducer arrays are spaced with respect to each other according to at least one of: a distance, and in close proximity.

In some embodiments of the invention, the at least one transducer array is configured in at least one of: a one-dimensional array (1D), a two dimensional array (2D), and a multi-dimensional (MD) grid pattern.

In some embodiments of the invention, the at least one transducer array comprises a grid pattern including at least one of: Cartesian and hexagonal patterns.

In some embodiments of the invention, the at least one transducer array comprises a sparse grid.

In some embodiments of the invention, the at least one transducer array includes at least one sub-array.

In some embodiments of the invention, the assembly includes an ultrasound beam-forming unit configured to produce ultrasound beam propagation wherein at least one of: at least one sub-array, the at least one array, a plurality of transducer arrays, and the at least one transducer are configured to provide beams consisting of at least one of: transmitting, and receiving, and the ultrasound processing unit includes a software module configured to process information from the provided beams.

In some embodiments of the invention, the ultrasound beam-forming unit is configured to produce ultrasound beam propagation in at least one of: two-way, and one-way, through the living body.

In some embodiments of the invention, the at least one transducer array includes at least one acoustic lens covering at least a portion of one of: at least one sub-array, the at least one array, a plurality of transducer arrays, and the at least one transducer.

In some embodiments of the invention, at least one of: at least one sub-array, the at least one array, a plurality of transducer arrays, and the at least one transducer, are configured to scan at least one of: a surface, and a volume.

In some embodiments of the invention, at least one of: at least one sub-array, the at least one array, a plurality of transducer arrays, and the at least one transducer, are configured to scan using at least one of: electronic scanning, and mechanical scanning.

In some embodiments of the invention, the mechanical scanning is performed by at least one of: swinging, rotating, and oscillating.

In some embodiments of the invention, the assembly includes at least one rail juxtaposed along the garment and at least one of: at least one sub-array, the at least one array, a plurality of transducer arrays, and the at least one transducer, are configured to move along the at least one rail.

In some embodiments of the invention, the movement is induced by at least one movement of: manual, and motorized.

In some embodiments of the invention, the at least one rail includes cogs operatively associated with at least one motor having at least one cog wheel configured to cause the movement along the at least one rail.

In some embodiments of the invention, the assembly includes at least one transducer-locating sensor operatively associated with the ultrasound processing unit, the at least one transducer-locating sensor occupying at least one position of: on the garment, and at a distance from the garment, and the ultrasound processing unit includes a software module configured to process spatial information from the at least one transducer-locating sensor.

In some embodiments of the invention, the at least one transducer-locating sensor comprises at least three transducer-locating sensors a distance from the garment and the ultrasound processing unit is configured to provide spatial triangulation of various points along the garment from the at least three transducer-locating sensors.

In some embodiments of the invention, the at least one transducer-locating sensor comprises at least one video camera configured to record location of various points along the garment.

In some embodiments of the invention, the at least one transducer-locating sensor occupying at least one position on the garment comprises at least one of: a magnetic sensor, an electro-magnetic sensor, and a radio frequency identification (RFID).

In some embodiments of the invention, the garment includes at least one fold that includes at least one of: an electronic sensor, and a mechanical sensor, configured to measure spatial angles along the at least one fold and transmit the spatial angles to the ultrasound processing unit.

In some embodiments of the invention, the ultrasound processing unit additionally includes a software module configured to process the spatial angles for at least one of: at least one sub-array, the at least one array, a plurality of transducer arrays, and the at least one transducer, located on each side of the one fold.

In some embodiments of the invention, the at least one transducer comprises one large ultrasonic array system and the ultrasound processing unit includes a software module configured to receive data and process data from the one large ultrasonic array system.

In some embodiments of the invention, the beam-forming unit is at least one of: included in the garment, and located a distance from the garment.

In some embodiments of the invention, the at least one ultrasound transducer comprises an "active" phased array which supports the generation of multiple receive beams in post ultrasound-receiving processing.

In some embodiments of the invention, the ultrasound processing unit includes a software module configured to operate the "active" phased array.

In some embodiments of the invention, the ultrasound beam-forming unit is configured to support at least one imaging mode including at least one of: reflection-based volume imaging, reflection-based ultrasound computed tomography (UCT), reflection-based ultrasound diffraction tomography (UDT), reflection-based beam pairs, transmission-based UCT, and transmission-based UDT.

In some embodiments of the invention, the ultrasound processing unit includes a software module configured to operate the ultrasound beam-forming unit such that the ultrasound processing unit receives and processes at least one mode including at least one of: transmitting, and receiving at least one beam concurrently.

In some embodiments of the invention, the ultrasound processing unit includes a software module configured to receive and process at least one dataset of: 1D, 2D, and 3D.

In some embodiments of the invention, the receiving comprises at least one of: time-dependent, and time-independent.

In some embodiments of the invention, the ultrasound processing unit includes a software module configured to receive and process repetitive scans of at least one of: a plane, and a volume, at predefined angular directions.

In some embodiments of the invention, the system includes at least one of: a plurality of sub-arrays, and the plurality of transducer arrays, and wherein the ultrasound processing unit includes a software module configured to compound signals received to produce at least one output dataset.

In some embodiments of the invention, the at least one dataset comprises at least two datasets which are combined, thereby achieving at least one of: extending a field of view, reducing speckle noise, improving signal-to-noise ratio, reducing shadowing artifacts, reducing clutter artifacts, enhancing spatial resolution, and enhancing image contrast.

In some embodiments of the invention, the at least two datasets are combined according to a predefined logic.

In some embodiments of the invention, the ultrasound processing unit includes a software module configured to provide computed tomography imaging and using a data analysis system based upon obtaining measurements using at least one of: cylindrical geometry, and spherical geometry.

In some embodiments of the invention, the ultrasound processing unit includes a software module-based process configured to compare reflections measured using opposite collinear beams to yield estimates of at least one of: a local attenuation coefficient, and a local speed of sound.

In some embodiments of the invention, the ultrasound processing unit includes a software module-based process configured to receive data from calibration beams, wherein the calibration beams include at least one of: transmit beams, and receive beams, and the process aligns the transmit beams and the receive beams.

In some embodiments of the invention, multiple strong reflectors are embedded in known positions along the garment, the strong reflectors including at least one of: different shapes, and different reflection characteristics, and the ultrasound processing unit includes a software module configured to discriminate between the strong reflectors.

In some embodiments of the invention, the ultrasound processing unit includes a software registration module configured to receive data which is one of: ultrasonic image based, sensor based, and ultrasonic image and sensor based.

In some embodiments of the invention, the ultrasound processing unit includes a software-based compounding module configured to produce output datasets from input datasets, wherein the input datasets comprise information from the provided beams, by: interpolating data for each input dataset to a coordinate grid of every output dataset, calculating a weighted mean over all input datasets per output grid point, using input datasets whose field of view covers the relevant grid point.

In some embodiments of the invention, interpolation is performed simultaneously to all input datasets.

In some embodiments of the invention, the weights for the weighted mean may be computed according to various criteria, the various criteria including at least one of: higher weights are assigned to input datasets whose nearby pixels provide better lateral resolution, weights are assigned in inverse proportion to the effective volume of the relevant pixels within an input dataset, weights are assigned according to a signal-to-noise ratio estimate per input dataset, and low weights are assigned to datasets in which the local signal level is significantly lower than in the other datasets.

In some embodiments of the invention, the ultrasound processing unit includes a software module-based process configured to provide at least one of: averaging, and weighted averaging, which are assigned to multiple datasets of several waveforms to reduce clutter effects.

In some embodiments of the invention, the assembly includes at least one transducer, producing different waveforms, wherein the ultrasound processing unit includes a software module-based process configured to provide various functions of datasets acquired by the at least one transducer at different waveforms that are calculated, thereby providing information with respect to local tissue type.

In some embodiments of the invention, statistical attributes of the waveform dependent data are utilized, the statistical attributes including at least one of: average, weighted average, standard deviation, and maximum to minimum ratio.

In some embodiments of the invention, the ultrasound processing unit is configured to receive input datasets acquired from multiple directions, and, for at least one small target region located in more than one of the input datasets, apply an elastic registration process to relevant measurements in the input datasets.

In some embodiments of the invention, the ultrasound processing unit extracts local attenuation coefficient measurements from outputs of the elastic registration process, wherein the elastic registration process is applied to at least two of the input datasets undergoing cumulative attenuation along different paths, wherein the cumulative attenuation results from local attenuation within the living body.

In some embodiments of the invention, the ultrasound processing unit extracts local speed of sound measurements from outputs of the elastic registration process, wherein the elastic registration process is applied to at least two of the input datasets undergoing cumulative time delays along different paths, wherein the cumulative time delays result from local attenuation within the living body.

In some embodiments of the invention, the elastic registration is performed on at least one of: pairs of opposite collinear beams, and groups of adjacent opposite collinear beams.

In some embodiments of the invention, in the pairs of opposite collinear beams, the registration is reduced to a single dimension and searching is done for specific patterns, including at least one of: maxima, minima, and other predefined patterns.

In some embodiments of the invention, the ultrasound processing unit includes a software module-based process configured to reduce clutter effects, including: acquiring at least one frame of data for the target volume, and for each sample range-gate at each beam position calculating a beam pattern for the current range, with respect to an applicable scanning apex, at all other beam positions, wherein the beam pattern is normalized so that the peak value is 1.0.

In some embodiments of the invention, the software module-based process is further configured to subtract from the sample range-gate measurement values at the same range, with respect to the applicable scanning apex, for all other beam positions, where each measurement value is multiplied by the corresponding beam pattern value.

In some embodiments of the invention, the software module-based process is further configured to subtract from the sample range-gate measurement values at the same range, with respect to the applicable scanning apex, for a group of other beam positions, where each measurement value is multiplied by the corresponding beam pattern value, and wherein the group of other beam positions comprises beam positions for which at least one value is high, the high value including at least one of: a measurement, and the beam pattern.

In some embodiments of the invention, the software module-based process performs iterative processing until a cessation criterion has been met.

In some embodiments of the invention, the ultrasound processing unit includes a software module configured to utilize data from at least one of: the at least one sub-array, the at least one array, the plurality of transducer arrays, and the at least one transducer, to provide pulsed-wave (PW) Doppler studies, wherein a full spectrum for a specific region is acquired from multiple directions, thus extending the information provided.

In some embodiments of the invention, the ultrasound processing unit includes a software module configured to utilize data from at least one of: the at least one sub-array, the at least one array, the plurality of transducer arrays, and the at least one transducer, to provide continuous-wave (CW) Doppler studies, wherein at least two intersecting beams, whose boresight directions over time may be at least one of: constant, and changing, are utilized to extract spatially dependent data.

In some embodiments of the invention, the ultrasound processing unit includes a software module configured to use Doppler shift measurements from at least two points of view and reconstruct a 2D projection of a 3D velocity vector corresponding to the dominant velocity for at least one pixel.

In some embodiments of the invention, the ultrasound processing unit includes a software module configured to receive Doppler shift measurements from at least three points of view and reconstruct a full 3D velocity vector for at least one pixel.

In some embodiments of the invention, an array of high intensity transducers is integrated into the ultrasound garment and at least one the high intensity transducer is at least one of: dedicated to high intensity focused ultrasound (HIFU) operation, and dedicated to imaging purposes.

In some embodiments of the invention, the ultrasound processing unit includes a software module configured to utilize at least one of: the local measurements of ultrasound attenuation, and the local measurements of speed of sound, to adaptively optimize the beam-forming parameters of the high intensity transducers.

In some embodiments of the invention, the ultrasound processing unit includes a software module configured to generate ultrasound computed tomography or ultrasound diffraction tomography images by geometrically transforming at least one of: scanning processing parameters, and signal processing parameters, to obtain samples equivalent to those obtained using at least one of: cylindrical geometry, and spherical geometry.

In some embodiments of the invention, geometric transformation includes introducing at least one equation of: phase delays, and time delays, to each transducer component, wherein the at least one equation refers to at least one of: transmission, and reception.

In some embodiments of the invention, the assembly includes at least one electromagnetic radiation source, the at least one electromagnetic radiation source occupying at least one position of: on the garment, and at a distance from the garment, and the at least one electromagnetic radiation source includes at least one of: light source, and radio-frequency (RF) source.

In some embodiments of the invention, the ultrasound processing unit includes a software module-based process configured to extract from ultrasonic reflections information regarding at least one of: local optical absorption, and local RF absorption.

In some embodiments of the invention, the ultrasound processing unit includes a software module-based process configured to perform at least one of the following techniques: ultrasound computed tomography, ultrasound computed tomography with the geometric transformation, attenuation correction using the local attenuation coefficient measurements, and time-delay correction using the local speed of sound measurements.

According to another aspect of some embodiments of the invention, there is provided, an ultrasound assembly, including: at least one ultrasound transducer array configured to be placed against a living body, an ultrasound beam-forming unit operatively associated with the at least one ultrasound transducer array, the ultrasound beam-forming unit configured to cause the at least one ultrasound transducer array to produce and receive at least one pair of opposite collinear beams that pass through the living body, an ultrasound processing unit operatively associated with the ultrasound beam-forming unit and configured to receive and compare the at least one pair of opposite collinear beams to yield estimates of at least one of: a local attenuation coefficient, and a local speed of sound.

In some embodiments of the invention, the ultrasound processing unit is configured to apply an elastic registration process to relevant measurements of the at least one pair of opposite collinear beams, and for each pair of opposite collinear beams perform at least one of: extract local attenuation coefficient measurements from outputs of the elastic registration process, wherein the pair of opposite collinear beams, to which the elastic registration is applied, undergoes cumulative attenuation along opposite beam paths, wherein the cumulative attenuation results from local attenuation within the living body, and extract local speed of sound measurements from outputs of the elastic registration process, wherein the pair of opposite collinear beams, to which the elastic registration is applied, undergoes cumulative time delays along opposite beam paths, wherein the cumulative time delays result from local variations in speed of sound within the living body.

In some embodiments of the invention, in pairs of opposite collinear beams, the registration is reduced to a single dimension and searching for specific patterns, including at least one of: maxima, minima, and other predefined patterns.

According to still another aspect of some embodiments of the invention, there is provided, an ultrasound assembly, including: at least one ultrasound transducer array configured to be placed against a living body, an ultrasound beam-forming unit operatively associated with the at least one ultrasound transducer array and configured to cause the at least one ultrasound transducer array to produce and receive multiple ultrasound signals through multiple small target regions in the living body, an ultrasound processing unit operatively associated with the ultrasound beam-forming unit and configured to compare the multiple ultrasound signals for each of the multiple small target regions to yield estimates of at least one of: a local attenuation coefficient, and a local speed of sound.

In some embodiments of the invention, the ultrasound processing unit includes a software module configured to apply an elastic registration process to the multiple ultrasound signals, and perform at least one of: extract local attenuation coefficient measurements from outputs of the elastic registration process, wherein the multiple ultrasound signals, to which the elastic registration is applied, undergo cumulative attenuation along different paths, wherein the cumulative attenuation results from local attenuation within the living body, and extract local speed of sound measurements from outputs of the elastic registration process, wherein the multiple ultrasound signals, to which the elastic registration is applied, undergo cumulative time delays along different paths, wherein the cumulative time delays result from local variations in speed of sound within the living body.

In some embodiments of the invention, the extraction is repeated for the multiple small target regions to provide a sound map of at least one region, including at least one of: a 2D region, and a 3D region.

In some embodiments of the invention, the extraction is repeated for the multiple small target regions to provide a 3D sound map and the software module is configured to: divide an output grid into layers taken at incremental ranges, determine a spatial map of at least one of: attenuation coefficients, and speeds of sound, and produce and correct a reflection coefficient map.

In some embodiments of the invention, the software module is additionally configured to produce and combine at least two of the following maps: reflection coefficients, attenuation coefficients, and speeds of sound, and provide tissue type classification data.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, software, or firmware; or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In embodiments of the invention, one or more tasks according to embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or an operator input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Figure 1A:
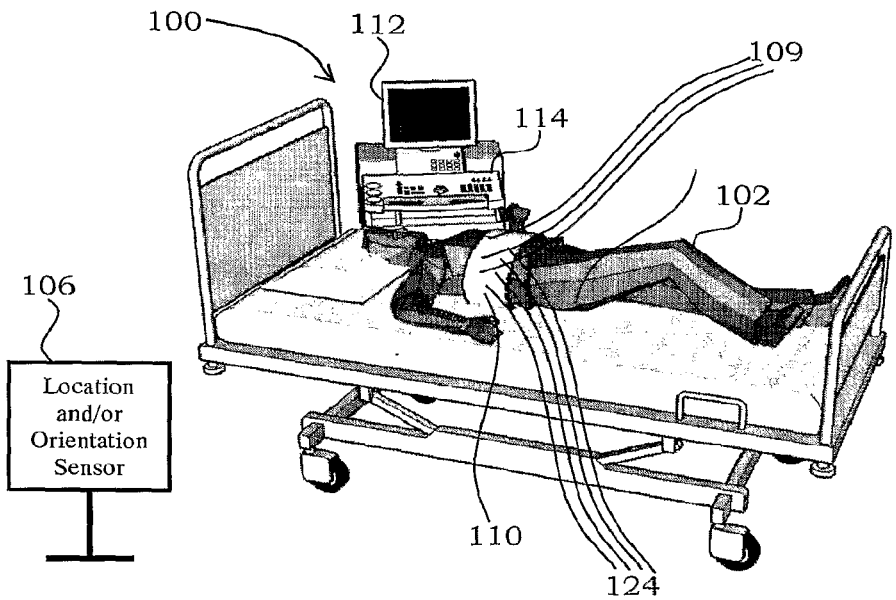
FIGS. 1A-1B show representations of an ultrasound system and operational flow chart, respectively, according to some embodiments of the invention.

DESCRIPTION OF SPECIFIC EMBODIMENTS
OF THE INVENTION

The present invention, in some embodiments thereof, relates to fixing the position of an ultrasound transducer with respect to a subject and, more particularly, but not exclusively, to fixing the position of an ultrasound transducer within a garment affixed to the subject.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Referring now to the drawings:

Ultrasonic Imaging System

In FIGS. 2-6, triangles stand for amplifiers or attenuators and crossed-out circles stand for phase shifters and/or true time-delay components. 'S.A.' stands for 'Sub-Array', 'Sig. Gen.' stands for 'Signal Generator', and $C_i^j$ is the j'th channel of sub-array i. When two or more lines intersect, connections are denoted by small black singular dots.

Triplets of black circle symbols without numbers represent copies of the units appearing in conjunction with the symbols, for example above and below the symbols.

Figure 1B:
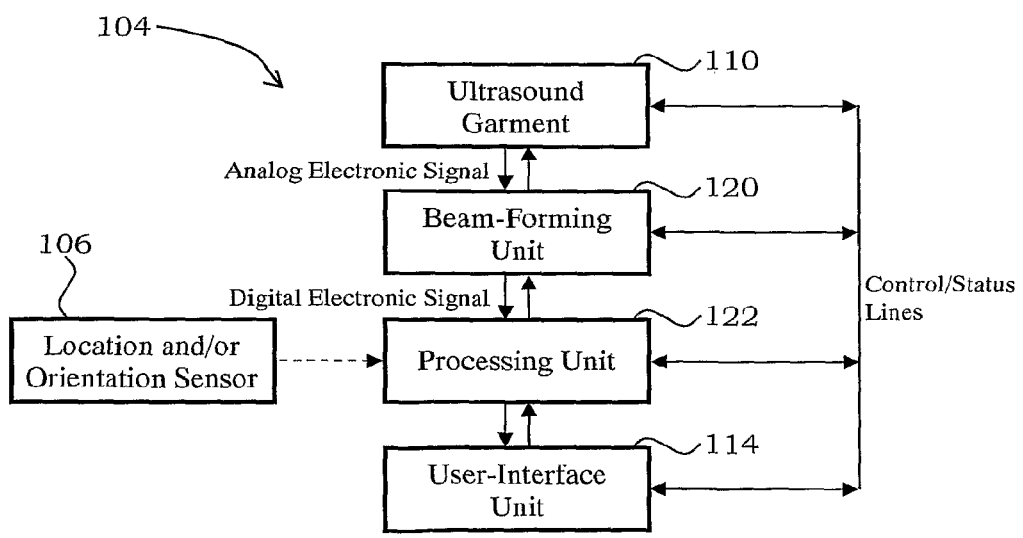

FIGS. 1A-1B show representations of an ultrasound (US) system 100 and operational flow chart 104 respectively which includes an ultrasound garment 110 affixed to a subject 102 and an ultrasound imager 112. While subject 102 is depicted as a human being, the present invention may be used and/or configured for use on non-human animals.

Ultrasound garment 110 includes transducers 124, alternatively referred to as transducer components 124, fixed in position in ultrasound garment 110 which, itself, is fixed in position with respect to subject 102.

Ultrasound garment 110 is alternatively referred to as affixed transducer array 110, stationary ultrasound garment 110 or stationary ultrasound transducer garment 110.

The inventor has discovered that transducers 124 having relatively known location and orientation may provide specific information that can contribute to the quality of the reconstructed images, for example on imager 112, as will be explained below.

US system 100 optionally includes a beam-forming unit 120; a processing unit 122 and an operator-interface unit 114, alternatively referred to as user-interface unit 114. In FIG. 1B, data lines are shown as one-directional arrows. Control/status lines are shown as two-directional arrows. Dashed lines relate to information which is optionally present in some embodiments of system 100.

Beam-forming unit 120 generates the electronic signal fed into ultrasound garment 110. Transducers 124 in ultrasound garment 110 transform the electronic signal into an ultrasonic signal, which within body of subject 102 undergoes, for example, attenuation, absorption, reflection, refraction, and dispersion.

The ultrasonic signal emanating from reflections and/or transmission through the body of subject 102 is then sensed by transducers 124 in ultrasound garment 110; which translate it into an electronic signal that is sampled by beam-forming unit 120.

The digitized information is then processed by processing unit 122. In embodiments, processing unit 122 also receives location and/or orientation information from ultrasound garment 110. Operator-interface unit 114 controls beam-forming unit 120; a processing unit 122, and also displays information to the operator on imager 112. In some embodiments, said control of operator-interface unit 114 may be performed through processing unit 122. Certain hardware configurations might combine ultrasound garment 110 and beam-forming unit 120 into a front-end unit.

Beam-Forming Unit Details

Beam-forming unit 120 has two basic roles alluded to above:
i. Generating the electronic signal which drives transmitting ultrasonic transducers 124, alternatively referred to as transducer components 124. In embodiments, beam-forming unit 120 provides a separate signal to each transmitting transducer 124 or group of transducers 124. In further embodiments, beam-forming unit 120 provides one or more driving signals for each array of transducers 124 or sub-array of transducers 124, as well as a set of parameters controlling the signal attenuation and/or time-delay for each transducer 124 or group of transducers. In the latter case, the signal attenuation and/or time-delays, required for forming the beams, are managed by ultrasound garment 110.

As used herein, the term "array" refers to an array of transducers 124; while the term "sub-array" refers to a sub-array of transducers 124 located within a larger array.

ii. Sampling the electronic signal produced by receiving ultrasonic transducers 124. Diverse signal types are sampled in different hardware configurations. In some cases, the signal reaching each transducer 124 or group of transducers 124 may be sampled. In other cases, one or more linear functions of some or all of transducers 124 in an array or sub-array may be measured. The linear combination may be performed by either ultrasound garment 110 or beam-forming unit 120. The linear weights for this linear combination can be predefined or calculated, and may be determined by beam-forming unit 120, by ultrasound garment 110 based on inputs from beam-forming unit 120, or by ultrasound garment 110 alone. Additionally or alternatively, the linear weights for the linear combination can be calculated by processing unit 122.

Garment Variations

There are a large number of designs and configuration of ultrasound garment 110. One ultrasound garment 110 embodiment, for example, is configured to partially or fully cover a certain body part, such as the abdomen or torso of subject 102.

Further, ultrasound garment 110 may be alternatively configured with different shapes; each configured to cover a different portion of a subject; for example a pelvis, arm, foot, and/or a head.

Additionally, ultrasound garment 110 optionally is configured to cover multiple body parts, or even the entire body of a subject. The many configurations possible for ultrasound garments 110 are easily recognized and appreciated by those familiar with the art of imaging.

In embodiments, ultrasound garment 110 is integrated into apparel, for example a belt, a shirt, or a pair of pants.

Additionally or alternatively, ultrasound garment 110 optionally includes two or more parts, allowing more than one possible assembly configuration, for example by separating one or more bands making up ultrasound garment 110 prior to fixing the transducers in place.

Optionally, the surface of ultrasound garment 110 is continuous and configured to be easily molded to a given body part, for example as an inflatable cuff around the arm.

Alternatively ultrasound garment 110 optionally includes some discontinuities. Additionally or alternatively, the surface of ultrasound garment 110 includes stretchable "seams" which can be stretched prior to fixation of the transducer positions.

In embodiments, ultrasound garment 110 optionally has an open configuration which may be adjustably closed around a body part. For example ultrasound garment 110 optionally includes a belt having adjustable diameter, with a closure system comprising Velcro material interposed between the belt surfaces. Additional closure systems optionally include straps, tape, or clips.

In embodiments, ultrasound garment 110 optionally includes ultrasound media designed for acoustic impedance matching between transducers 124 and the body surface of subject 102. Such ultrasound media optionally, for example, include gel packs, covering parts of, or the entire inner surface of the apparatus. The gel packs optionally are disposable or refillable. The media used for acoustic impedance matching optionally includes a gel. Additionally or alternatively, the media optionally includes a gas, liquid, or solid.

Garment Fixation

In embodiments, one or more fixation devices, such as straps, sticky patches or vacuum patches, optionally are used for keeping ultrasound garment 110 affixed in place.

In other embodiments, the fixation device is a part of transducers 124. For example, sticky surfaces or vacuum generating surfaces optionally are used to maintain transducers in fixed positions.

Another option for maintaining position of transducers 124 is the addition of a gas pocket providing negative pressure between the US transducer array and the body surface, for example, along the inner surface of the apparatus. The pressure within such a gas pocket optionally is adjusted to obtain a tighter or a looser fit of ultrasound garment 110.

In embodiments, the gas pocket is located along the outer surface of the apparatus and positive pressure, for example through inflation of the gas pocket, causes the transducers to be fixed in place.

Transducer Configuration

In some embodiments, ultrasound garment 110 optionally includes a large US transducer array; which may be divided into multiple sub-arrays. Such sub-arrays optionally overlap each other in some configurations, while in other configurations the sub-arrays are separate. In either case, the sub-arrays activation can be predefined or adaptively allocated by the imaging system.

The transducer array may, for example, comprise piezoelectric crystals.

The transmitting and/or receiving transducer components 124 optionally cover the entire ultrasound garment. Alternatively, the transmitting and/or receiving transducer components 124 optionally cover portions of ultrasound garment 110.

In embodiments, the transducer array covers ultrasound garment 110 uniformly or non-uniformly.

Optionally, in embodiments, pluralities of transducer arrays are used. The arrays optionally are placed in close proximity to one another. Alternatively, the pluralities of transducer arrays optionally are placed at a distance from each other.

In some embodiments, each of the multiple arrays has a separate casing or housing, and even a separate driving unit. In other embodiments, several arrays are housed together.

Irrespective of the number of arrays or sub-arrays, each array or sub-array optionally includes one or more transmitting and/or receiving transducer components 124, ordered in a one-dimensional (1D), two-dimensional (2D), or multi-dimensional (MD) grid; wherein the grid pattern is Cartesian.

Alternatively, the grid pattern has a different pattern, for example, one or more hexagonal patterns. In still further embodiments, sparse grids are utilized. In some embodiments, one or more acoustic lenses optionally cover a sub-array, an array, or a group of arrays, either partially or fully, for example to adjust the acoustic beam dimensions.

Each US transducer array and/or sub-array is optionally used to acquire ultrasonic information regarding a certain line, a surface, or a volume within the subject's body.

An array or sub-array optionally scans a surface or a volume electronically and/or mechanically. Said mechanical scanning may be performed, for example, by swinging, rotating, or oscillating the array, the sub-array, or even a group of transducers within the array or sub-array. In some cases, scanning is optionally electronic in a first axis and mechanical in a second axis.

Data acquisition is optionally performed over a short period of time. Alternatively, data acquisition is performed several times over a longer period of time, thereby providing time-dependent information.

In some embodiments, some or all of the transducer components 124, sub-arrays or arrays, are moved with respect to the surface of ultrasound garment 110, for example so as to enhance data acquisition flexibility.

In embodiments, transducer components 124, sub-arrays or arrays can be moved manually, for example, along special railings. In embodiments, detachable arrays are optionally fixed to multiple fixation points. Alternatively, motors may be utilized to change the location of the arrays, for example using rails with cog-wheels.

Location Sensors

Additionally or alternatively, ultrasound garment 110 includes one or more location sensors or location sensor arrays 109 designed to provide data regarding the relative spatial location and/or orientation of different regions or transducer components 124 of ultrasound garment 110.

The location sensors or location sensor arrays 109 optionally utilize one or more of the many locating sensor technologies known in the art, for example:

i. In cases where ultrasound garment 110 has well defined axes allowing folding, whether or not taking the form of actual axes, the spatial angle between the surfaces on both sides of such axes is optionally measured by electric sensors comprising, for example, location sensor arrays 109.

ii. An optical stand-alone array 106 including one or more video cameras placed beside ultrasound garment 110 optionally allows spatial triangulation of various points along ultrasound garment 110.

iii. Magnetic or electro-magnetic location sensor arrays 109 attached to multiple locations along ultrasound garment 110 and/or placed as stand-alone arrays 106;

iv. A plurality of radio frequency identification (RFID) chips location sensor arrays 109 mounted on ultrasound garment 110 which may optionally transmit to a base station (not shown).

As is known in the art, a group of three or more location sensors 109, mounted on a rigid surface, for example an ultrasonic array or a sub-array; allows accurate estimation of both the location and orientation of that surface.

Conversely, if ultrasound garment 110 has known axes with degrees of freedom, less than three location sensors 109 may be required to fully estimate the spatial location and orientation of each ultrasonic array or sub-array.

As described above, ultrasound transducers 124 are optionally configured as having combined receiving and transmitting transducers. However, ultrasound transducers 124 may be configured with separate receiving and transmitting transducers. The following narration describes just one of the many configurations of generating signals fed to transducers 124 and analyzing the received signals.

Single Large Ultrasonic Array

Figure 2:
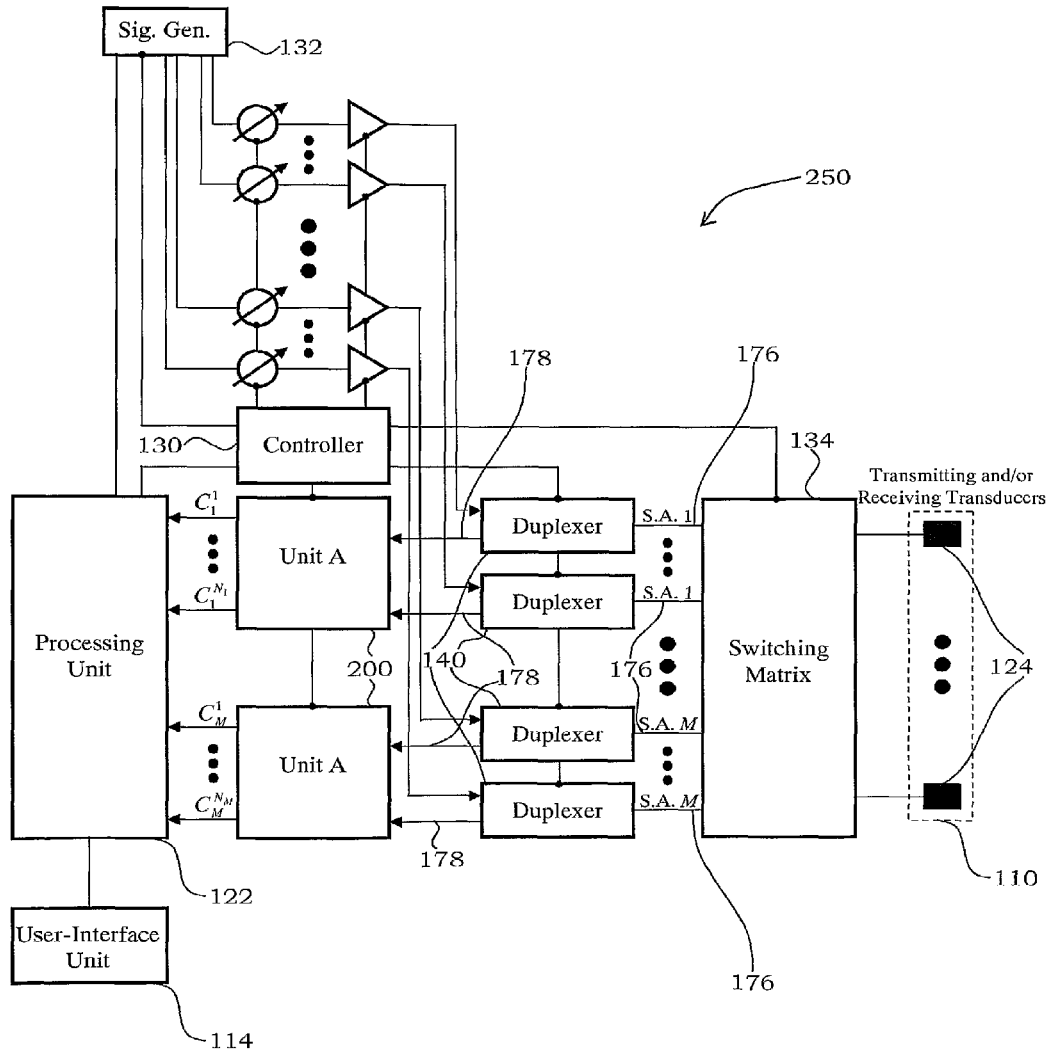
FIG. 2 shows a single large ultrasonic array system, according to some embodiments of the invention.

FIG. 2 is an embodiment of a single large ultrasonic array system 250, which includes ultrasound garment 110.

Transducers 124 comprise a large ultrasonic array system which produce and/or receive ultrasound signals.

As a result of passing signals through a switching matrix 134, multiple sub-arrays are defined.

The result comprises M adaptively defined sub-arrays of transducer 124 where each m'th sub-array (m varies between 1 and M) has $N_m$ receive datasets, and therefore, for example, $N_m$ analog-to-digital (A/D) converters.

Ultrasound garment 110 and beam-forming unit 120, which includes components besides ultrasound garment 110, processing unit 122, and operator-interface unit 114, may be used in configurations where the reception and transmission transducers 124 are combined or separate.

On transmit; the waveform produced by signal generator 132 optionally passes through amplifiers and/or attenuators, as well as phase shifter and/or true time-delay devices, as shown in the figure by triangles, and crossed-out circles as noted above.

This signal is fed to the transmitting transducer components 124 through a switching matrix 134, which adaptively allocates transmitting and/or receiving transducer components 124 to data lines 176 as defined by controller 130.

On receive; the signal from each receiving transducer component 124 is directed to the appropriate duplexer 140 using a controllable switching matrix 134, and may be amplified and/or attenuated, and in some cases undergo phase shifts and/or true-time delays.

Figure 3:
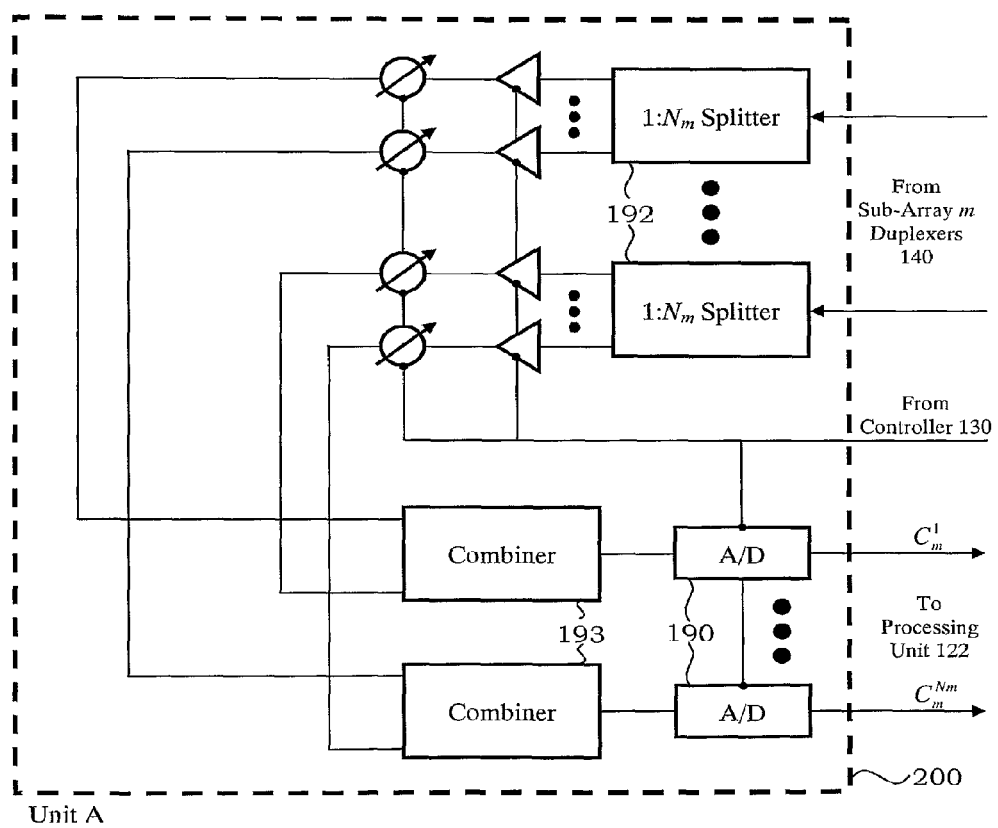
FIG. 3 shows details of a portion of FIG. 2, according to some embodiments of the invention.

The resulting signal from duplexers 140 enters Unit A 200 through data lines 178, as seen in detail in FIG. 3. In Unit A 200, $1:N_m$ splitters 192 split signals from duplexers 140 (where m is the sub-array index). For every $n_m$ between 1 and $N_m$, the $n_m$'th output of each splitter can be further amplified or attenuated to adjust the sub-array's apodization pattern, and can also be fed through a phase shifter or a time-delay device. The signals then enter the $n_m$'th combiner 193.

The outputs of each combiner 193 are sampled by an A/D converter 190, and transferred to processing unit 122. Some or all of the amplifiers, attenuators, phase shifters, and true time-delay devices may be directed by controller 130.

In embodiments, the amplification/attenuation and/or the phase shift/time-delay may be performed in two or more stages, located on one or two sides of duplexers 140 (FIG. 2). Furthermore, both signal generator 132 and controller 130 or controllers 130 may be managed (controlled) by operator-interface unit 114 and/or processing unit 122.

Signals fed to and/or received from ultrasound transducers 124 may be generated and/or analyzed in a variety of circuit configurations. The following narration describes just some of the many options for these circuit configurations.

Exemplary Circuit Configurations

Figure 4:
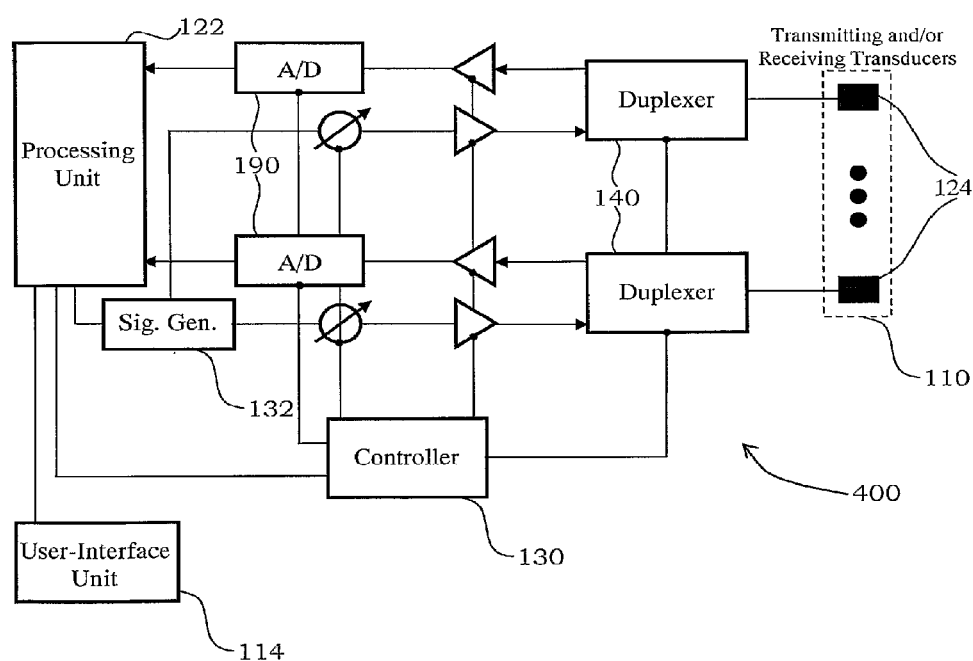
FIG. 4 shows an active phased array system, according to some embodiments of the invention.

FIG. 4 is an embodiment of an active phased array system 400, where an A/D converter 190 is assigned to each transmitting and/or receiving transducer component 124 or group of transducer components 124. Such an "active" phased array supports the generation of multiple receive beams in post-processing, without prior beam definition.

On transmit, the waveform produced by signal generator 132 passes through amplifiers and/or attenuators, as well as phase shifters and/or true time-delay devices, the parameters for all of which may be controllable by a controller 130. This signal is fed to transmitting transducer components 124.

On receive, the received signal may be amplified and/or attenuated, and may also undergo phase shifts and/or true-time delays. The resulting signal is sampled by A/D converter 190, and transferred to processing unit 122. Both signal generator 132 and controller 130 may be managed by operator-interface unit 114 and/or processing unit 122.

Figure 5:
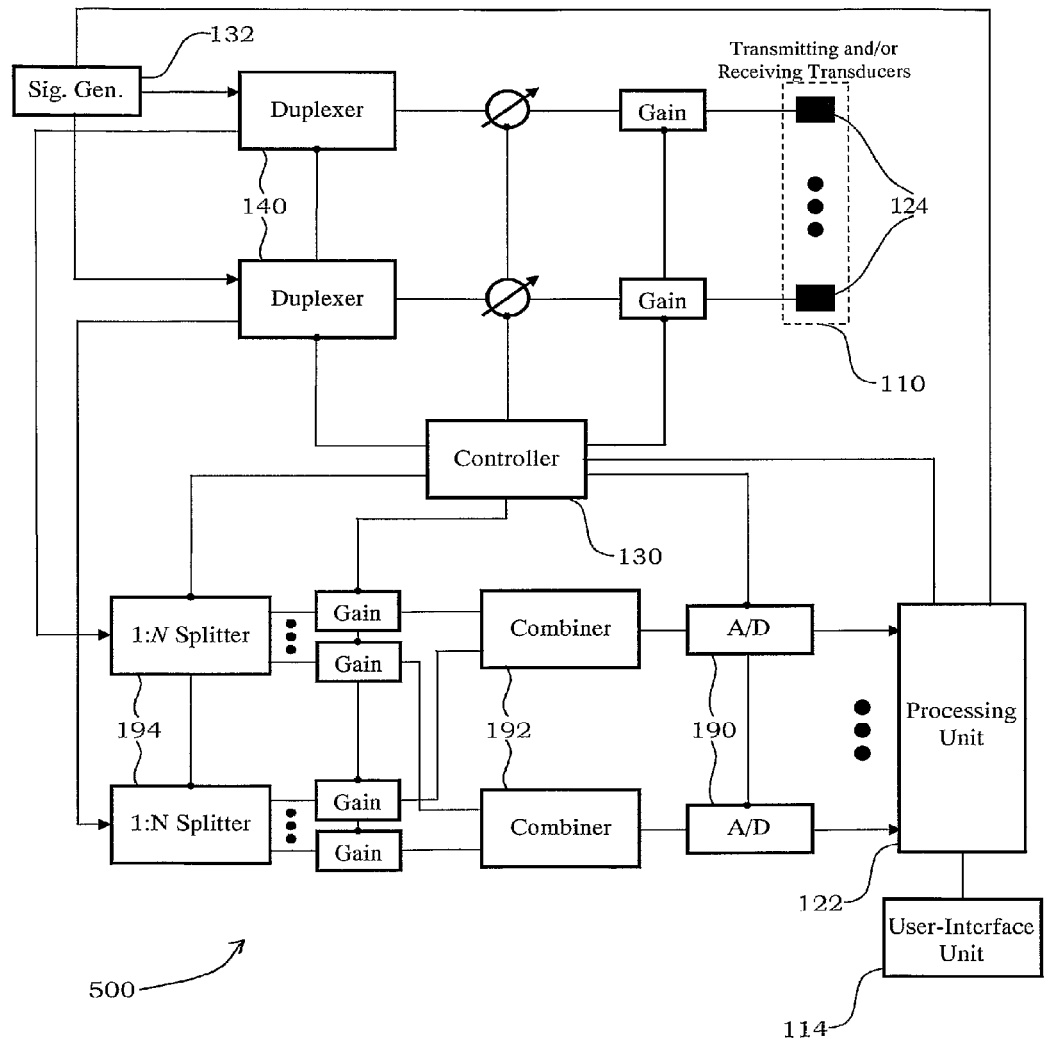
FIG. 5 shows a single sub-array system, according to some embodiments of the invention. In some configurations, the ultrasound system may include a plurality of such sub-arrays.

FIG. 5 is an embodiment of a single sub-array system 500. In some configurations, the system may include a plurality of such sub-arrays. However, some or all of the following units may not necessarily be duplicated: the controller 130, the signal generator 132, the processing unit 122, and the user-interface unit 114.

On receive, the signal from each receiving transducer component 124 may be amplified and/or attenuated, and may also undergo phase shifts and/or true-time delays. The resulting signal for each receiving transducer component 124 enters a 1:N splitter 194 (N may vary from one sub-array to another). For every n between 1 and N, the n'th output of each splitter can be further amplified or attenuated to adjust the sub-array's apodization pattern, and can also undergo phase shifts and/or true-time delays. It then enters the n'th combiner.

The outputs of each combiner 192 are sampled by A/D converter 190, and transferred to processing unit 122.

Both signal generator 132 and controller 130 may be managed by operator-interface unit 114 and/or processing unit 122. In some embodiments, the amplification/attenuation and/or the phase shift/time-delay may be performed in two or more stages, located on one or two sides of the duplexers.

Figure 6:
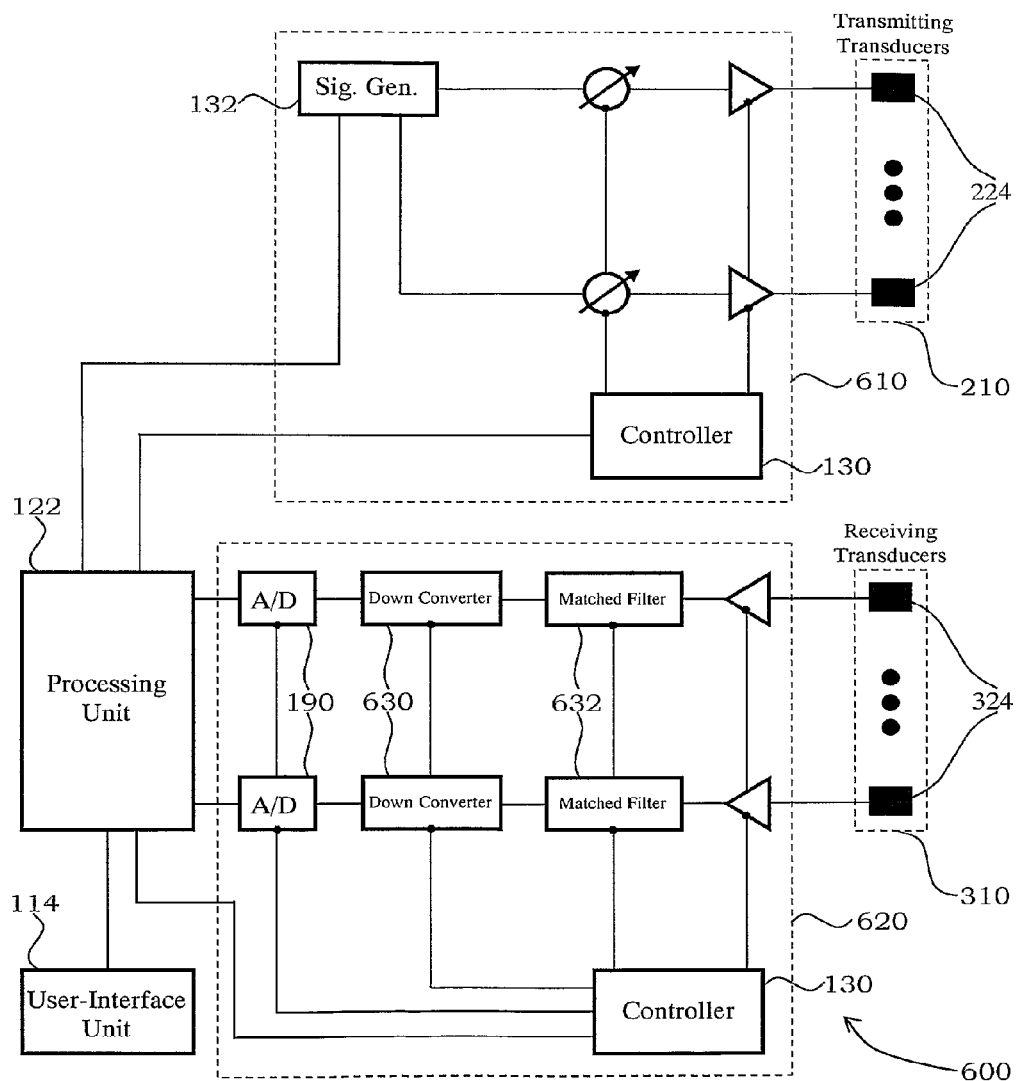
FIG. 6 shows active phased array systems, according to some embodiments of the invention.

In all configurations, some arrays or sub-arrays can be used only for transmitting or only for receiving, in which case duplexers are not necessary. FIG. 6 is an embodiment of an "active" phased arrays system 600, including a dedicated transmitter 610 and a dedicated receiver 620.

Dedicated transmitter 610 and dedicated receiver 620 have application, for example, in transmission mode UCT, and in ultrasound diffraction tomography (UDT) imaging modes which utilize pairs of sub-arrays 210 and 310.

Each such pair includes a transmitting sub-array 224 and a receiving sub-array 324, which may, for example, generate opposite collinear beams. Some or all receiving sub-arrays 324 may also receive reflected or transmitted signals generated by other sub-arrays (not shown).

It should be understood that FIGS. 2-6 optionally include location and/or orientation sensors 106 and 109, seen in FIG. 1, and respective processing.

In embodiments, a down-converter 630 may be added prior to the A/D converter, subtracting the frequency of the signal carrier provided by signal generator 132, which may be constant or time dependent. Alternatively, down-converter 630 may set the center frequency to one of the signal carrier frequency's harmonics.

In other embodiments, the measured analog signal may be correlated to the output of signal generator 132 in which a matched filter 632 is optionally utilized, so as to provide pulse compression.

In some embodiments, the gain applied prior to sampling by the A/D converter may be automatically adjusted based on the measured signal (a technique called "adaptive gain control"). The gain can also be time dependent ("time-gain control"), in order to decrease the dynamic range to be sampled, thus reducing the number of bits required by the A/D. Furthermore, in certain embodiments, the A/D converter may produce real samples, whereas in other embodiments complex measurements are made.

Technologies relating to transducers 124 may include a variety of technologies other than planar arrays or phased arrays, in which case the term "sub-array" should be interpreted as an ultrasound source and/or detector. The term "sub-array" may also indicate a first separate array in conjunction with a second separate array.

Processing unit 122 may employ any technology known in the art. In some cases, it may be PC-based or any other suitable computing platform. Additionally or alternatively, one or more digital signal processors (DSPs), application-specific integrated circuits (ASICs) and/or field-programmable gate array (FPGA) chips may be used. Thus, processing unit 122 may include hardware components and/or software modules.

Operator-interface unit 114 controls the other units according to the operator's requirements. This may be performed either directly or through processing unit 122.

Operator-interface unit 114 may also receive status signals from the other units. In addition, this unit displays the operator selected information, which can consist of alphanumeric information, measured quantitative parameters, 2D or 3D anatomic and/or parametric images, various sections or projections of anatomic and/or parametric images and the like.

Images and parameters may be time dependent. Pseudo-colors may be used to describe functions of different parameters or a combination of two or more parameters, for example the videointensity may describe one parameter whereas the hue may describe another. Any display type, for example a computer monitor or a 3D holographic display, may be used for that purpose.

In some embodiments, some or all of the data and/or control cables may be replaced with wireless communication of various types, using, for example, Bluetooth of WIFI technology.

Adjustable Transducer Array Garment

Ultrasound garment 110 optionally uses a garment that includes ultrasound transducer ports at multiple locations, to which the operator selectively chooses and hooks up a variable number of transducers.

The transducer port locations may be predefined, manually adjustable, or adjustable using a motor. Motorized adjustment may be performed during an examination, for automatically moving one or more probes over a surface, scanning a selected volume. Motorized adjustment may also be performed before or after an examination, or during system mode transition. Adjustable transducer array garment optionally includes a location and/or orientation sensor array described above.

The data obtained at multiple locations are recorded by the ultrasound imaging system, and then analyzed either online or offline, using the techniques described herein.

Beam-Forming and Waveforms

Beam-forming may be described in terms of complex weights assigned to different transducers 124 of a transmitting and/or receiving sub-array. The complex weights are implemented, for example, by applying gain and/or attenuation, phase delays and/or time delays.

The complex weights may follow any suitable pattern. For example, the pattern of the gain of the transducer components 124 may follow a one-dimensional or a two-dimensional Hamming window. In some embodiments, the phase setting on transmit should be set to provide one or more focal points. In this context, a focal point is a spatial location at which the phases of the signals generated by all relevant transmitting transducer components 124 is equal to a certain constant, for example 0.

In further embodiments, the phase setting on receive should provide dynamic focusing, i.e., the phases for each sample (range-gate) are set so as to assure that the overall time or phase delay along all paths between the volume corresponding to the current sample and each receiving transducer component 124 is equal to a certain constant; for example as described by Angelsen B A J; "Ultrasound Imaging—Waves, Signals and Signal Processing"; Emantec A S, Trondheim, Norway 2000; I:1.34-1.44.

The system may utilize any waveform known in the art, including both pulsed wave (PW) and continuous wave (CW) transmission. In embodiments, rectangular pulses may be used. Optionally, coded excitation techniques may be used, such as linear or non-linear frequency modulation; binary sequences, for example, Barker codes, Allomorphic forms and complementary sequences; and poly-phase codes; as described by Skolnik M I; "Radar Handbook"; McGraw-Hill, Boston, Mass. 1990; 10.1-10.39.

Furthermore, in embodiments, different coded excitation techniques or approximately orthogonal sequences of the same coded excitation technique may be fed to different transducer components. This allows, for example, dynamic focusing and/or dynamic aperture setting on transmit, as mentioned by Zheng Y, Silverstein S D; "Novel Transmit Aperture for Very Large Depth of Focus in Medical Ultrasound B-scan"; IEEE Transactions on Ultrasonics, Ferroelectrics, and Frequency Control 2006; 53:1079-1087.

System Modes

Numerous configurations of transmission and/or reception transducer component allocations may be considered for ultrasound garment 110-based systems. At any given time, P sub-arrays may be assigned to transmit and Q sub-arrays may be assigned to receive; P and Q are parameters which may or may not be equal, and can change over time. Some of these sub-arrays may perform both transmission and reception.

Furthermore, a certain receiving transducer sub-array may provide multiple receive datasets; for example, use multiple A/D converters; each of which can relate to different beam configurations.

Different beam configuration include, for example, differences in beam width, boresight direction, receive gain, and/or central frequency.

In some embodiments, one or more of the following basic modes, described hereinbelow, can be supported:
  i. Reflection-based volume imaging.
  ii. Reflection-based UCT.
  iii. Reflection-based UDT.
  iv. Reflection-based beam pairs.
  v. Transmission-based UCT.
  vi. Transmission-based UDT.

The reflection-based volume imaging and the reflection-based beam pairs mode are also referred to as the "fundamental reflection modes".

For each mode, data for the target volume or for parts of that volume may be obtained once. Alternatively, it may be collected as a function of time. When time-dependent information is gathered for organs showing cyclic motion, such as the heart, applicable measurable biological signals, for example electrocardiography signals, may be utilized to improve image quality. Such procedures are usually referred to as gating techniques. For example, the cycle may be divided into K intervals, and the data for each interval may be integrated over multiple consecutive cycles.

In some cases, data may be collected for partial volumes, which may be defined by the operator or selected automatically following various criteria. The partial volume covered may also change over time. Data acquisition for partial volumes usually requires using fewer beams to cover the scanned volume, and thus allows increased refresh rates, which are especially useful in applications where the target organ moves over time, for example cardiac imaging or gastrointestinal imaging.

In further embodiments, two or more of the above described imaging modes, for example reflection-based volume imaging and transmission-based UCT may be combined, and applied in either concurrent or alternating fashion. In such cases, the processes for the two or more imaging modes will be applied.

Additionally or alternatively, tailored processes may be defined for these combined modes. For instance, transmission-based measurements, examples for which are attenuation and time delay measurements, may provide a reference for various reflection-based processes, performing operations such as attenuation correction or corrections for speed of sound variability. Special display configurations may be devised for the combined modes, providing the operator with various functions or representations of the information obtained.

Transmitting and/or receiving a plurality of beams concurrently may reduce the overall time required to cover the target volume or partial volume. However, when two or more beams are transmitted at the same time or approximately at the same time, especially if the beams' main-lobes cover spatially adjacent volumes, some mutual interference may occur. In order to prevent such mutual interference, different concurrent beams may use different transmission frequencies.

Additionally or alternatively, concurrent beams may use different coded excitation patterns, for example dissimilar linear frequency modulation patterns.

Reflection Versus Transmission Imaging

As mentioned hereinabove, reflection modes provide an array of time dependent echo measurements. Given the approximate local speed of sound, time dependence may be translated into range dependence. These measurements are correlated to the local reflection coefficient, but also are affected by the two-way cumulative attenuation along the beam, up to the relevant reflecting volume of tissue.

Conversely, transmission modes usually provide only two scalar parameters for each beam—an estimate of the speed of sound, and the total signal attenuation along a beam.

Furthermore, the beam configuration for reflection and transmission modes is different. In reflection modes, the transmitting sub-array is often used for receiving as well. In some cases, additional adjacent sub-arrays, located on the same side of the subject, are used to receive the reflected signal as well. In comparison, in transmission modes, one or more receiving sub-arrays are assigned to each transmitting array. The transmitting and receiving sub-arrays are located on opposite sides of the subject.

In transmission-based UCT, a receive beam should be paired with each transmit beam. The two beams should be collinear or close to collinear, and also temporally synchronized.

Reflection-Based Volume Imaging

This mode is based on acquiring 1D, 2D, or 3D datasets, which may or may not be time-dependent, by multiple sub-arrays (or arrays). Each sub-array may be 1D, 2D, or MD, and can scan a target volume using any scanning pattern. The origin of all beams produced by a sub-array is referred to as the "phase center" or the "scanning apex". In some cases, one or more transmitting and/or receiving transducer components may be included in more than one sub-array. In some embodiments, the system repetitively scans a plane or a volume at predefined angular directions, for example equidistant azimuth and/or elevation angles, using one or more scanning apexes.

The data acquired by all sub-arrays is compounded to produce one or more output datasets. In some embodiments, an output dataset may cover the combined volume of all acquired datasets, thus extending the field of view. In some further embodiments, only regions covered by several sub-arrays (or "views"), as determined according to a predefined logic, are included in the output datasets.

Ultrasound Computed Tomography (UCT)

The inventor has discovered that ultrasound garments may have application in UCT and UDT imaging. The following description presents just some of the many possible means of extracting information to provide UCT and UDT imaging data.

Currently available reflection mode or transmission mode UCT systems usually utilize cylindrical geometry, i.e., the transmitting and/or receiving sub-arrays are placed on the surface of an approximate cylinder. Ultrasound garment 110 systems provide a more generalized geometry, which usually cannot be determined prior to outfitting the subject with the system.

In order to solve the new, more complex geometry, the inverse problem equations may be rewritten and solved. Additionally or alternatively, one can adjust the scanning and/or signal processing parameters to obtain samples equivalent to those obtained using, for example, cylindrical or spherical geometry (this method is referred to hereinbelow as the "geometry emulation algorithm"). Once these adjustments are made, any inverse problem method, and especially any UCT technique, which are known in the art, may be applied. These methods include, for example, iterative back-projection, filtered back-projection, and analytic reconstruction; for example as described by Louis A K; "Medical Imaging: State of the Art and Future Development"; Inverse Problems 1992; 8:709-738.

The geometry transformation may be performed by introducing phase and/or time-delays to each transmitting and/or receiving transducer component, which are set so as to emulate the transmission and/or reception of the signal from a transducer component placed on the surface of a pre-selected 3D geometric shape. In an embodiment, this shape is a cylinder, whose diameter is equal to or greater than the maximal distance between any pair of sub-arrays (or transmitting/receiving transducer components). The one-way (transmit or receive) time-delay $\Delta t$ required for effectively translating the location of a transmitting and/or receiving transducer component, whose location with respect to the center of the current range-gate is $\vec{r}$, to a new location $\vec{r}\,'$, given in the same coordinate system, is:

$$\Delta t = \frac{(|\vec{r}\,'| - |\vec{r}|)}{c}$$

where c is the speed of sound in the medium. Similarly, the one-way phase delay $\Delta\phi$ is given by:

$$\Delta\phi = 2\pi \bmod\left[\frac{(|\vec{r}\,'| - |\vec{r}|)}{\lambda}, 1\right]$$

where $\lambda$ is the transmitted or received wavelength and 'mod' stands for the modulus operator. If the same transducer component both transmits and receives, the time-delay and/or phase delay should be doubled.

The effective location of each transmitting and/or receiving transducer component may be set according to different criteria. For example, in reflection mode, for each range-gate, the transducer component may be effectively placed at the intersection point between the selected 3D geometric shape and a line connecting its actual location with the center of the range-gate, as explained below with respect to FIG. 7. Another solution is translating the effective location of the to transmitting and/or receiving transducer component to the surface of the 3D geometric shape along a line parallel to the beam's boresight, which goes through the transducer component's actual location.

Transducer Component Translation

Figure 7:
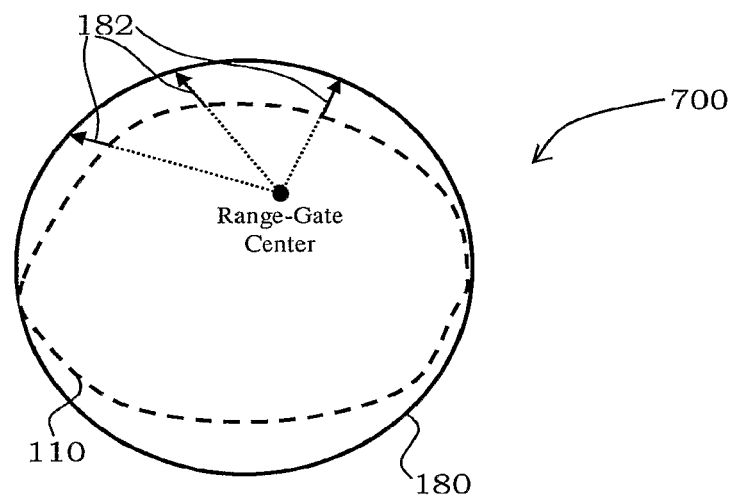
FIG. 7 shows effective transducer geometry translation, according to some embodiments of the invention.

FIG. 7 shows a configuration of effective transmitting and/or receiving transducer component translation 700, according to an embodiment of the present invention. For convenience purposes, a 2D case is used. The actual surface of ultrasound garment 110 is shown as a black dashed line, whereas a selected 3D geometric shape 180 is shown as a black solid line. Arrows 182 show the translation required in this case for several transducer component locations. Dotted lines connect the transducer components with the center of the range-gate.

This transformation requires knowing the actual location and/or orientation of each transmitting and/or receiving transducer component. This information may be based on a sensor array, but may also use other techniques, described in the "Coordinate System Registration" subsection below. Once this information is available, it may also be used during reconstruction as a constraint over the solution: there is no reflection or attenuation outside the actual surface of ultrasound garment 110.

Additionally or alternatively, dummy '0' measurements may be added in reflection modes for regions outside the actual surface of ultrasound garment 110.

In addition, this transformation changes the effective area of the sub-array, and may therefore affect beam width (in both axes), angular resolution, and signal-to-noise ratio (SNR). In some embodiments, the shape and dimensions of the sub-array may be adjusted to provide more homogeneous angular resolution and SNR over different beams.

Ultrasound Diffraction Tomography (UDT)

Unlike UCT, UDT requires that for each transmit beam, multiple measurements would be made on receive, using a plurality of phase centers and/or beam directions.

As in the case of UCT, one may solve the new inverse problem equations, and/or adjust the system to produce data equivalent to that obtained in cylindrical geometry platforms (or platforms of other geometries), using the techniques described in the previous subsection "Transducer Component Translation".

Beam configuration design for UDT modes is often quite complex. The phase center location and orientation of the various receive beams with respect to the relevant transmit beam may be constant, but it may also change over spatial location or time. For instance, the spatial angles formed between the transmit beam and each of the relevant receive beams may be kept constant. Another possibility is to keep a constant distance between the phase centers over ultrasound garment 110 surface. Moreover, in some embodiments, the orientation of the receive beams may adaptively change during data acquisition per pulse. For example, all receive beams may be directed at a point along the transmit beam, which is scanned over time.

Reflection-Based Beam Pairs

In embodiments, one can obtain additional information by comparing the reflections measured along opposite collinear beams. Examples for such additional information, which can be obtained using methods described hereinbelow, are estimates of the local attenuation coefficient, or local speed of sound.

Generating opposite collinear beams in ultrasound garment 110-based systems, where the data acquisition geometry changes between different subject 102s and even different examinations, requires precise knowledge of the relative location and/or orientation of different transducer components and/or sub-arrays, as well as accurate control over the scanning apex location, and the directionality of transmit and receive beams. Methods for evaluating the location and/or orientation of transducer components and/or sub-arrays are described in the "Coordinate System Registration" subsection below. These methods also include special calibration beams, which may be utilized for collinearity optimization. Various ultrasound garment 110 hardware configurations, as described hereinabove, can provide adequate control over apex location and beam directionality.

Applicable Processes

In various embodiments, one or more of the following processes may be applied to the acquired data:
i. Processing per receive dataset—processing applied directly to each receive dataset, i.e., to the outputs of each A/D converter.
ii. Coordinate system registration—matching the coordinate systems of data acquired by multiple sub-arrays (or arrays) or by one or more sub-arrays at different time frames.
iii. Compounding—combining the data obtained from multiple sub-arrays or from one or more sub-arrays at different time frames to form one or more new datasets.
iv. Further processing may be applied for display purposes, according to the operator's requirements.

Examples of such processes are given in the current section. It should be emphasized that the use of all these processes is not restricted to ultrasound garment 110 systems as described herein, but rather may be expanded to any ultrasound imaging system where data is acquired at multiple positions and/or tilts, using one or more imaging probes, and the data from the multiple positions and/or tilts is combined and compounded to generate one or more datasets, which may be one-, two-, or three-dimensional, and either time dependent or time independent.

Processing per Receive Dataset

The processing per receive dataset may use any suitable technique known in the art. Some processing steps are:
i. Logarithmic compression—the magnitude or squared magnitude of the sampled data may be converted into logarithmic units, for example decibels, in order to reduce the dynamic range.
ii. Time-gain control (TGC)—time (range) dependent gain corrections may be applied. These corrections may be performed in hardware, software, or a combination thereof. The parameters of these corrections may be set by the operator, but may also be automatically determined.
iii. Dynamic range windowing—mapping all values to a range between predefined minimal and maximal values. Values lower than a certain threshold may be set to the minimal value, whereas values higher than another threshold may be set to the maximal value.
iv. Brightness transfer function (BTF)—applying certain predefined or adjustable functions to the values. These functions are usually aimed at improving the contrast for specific ranges of signal level.

Coordinate System Registration

As mentioned above, registration may be defined as a process mapping any point in one coordinate system to the corresponding point in another system. This mapping may be spatial and/or temporal. Ultrasound garment 110-based systems provide three potential sources for location and/or orientation information, each of which may provide time dependent information:
1) The sensor array, if included in the system, provides direct estimates of location and/or orientation for multiple sub-array or array transducer components. However, the accuracy of these estimates is fairly limited.
2) A higher degree of information accuracy may be obtained with special beam configurations ("calibration beams"). In some cases, the calibration beam design may be founded on the assumption that when a transmit beam and a receive beam are well aligned, the transmission mode and perhaps the reflection mode signal levels are expected to be higher than in other, non-aligned scenarios. Configurations include:

i) In transmission UCT mode, several receive beams, having slightly different orientations and/or apexes, may be used per transmit beam. By selecting the receive beam producing the highest signal intensity, one can align the receive beam with the transmit beam. Such measurements can also be performed iteratively, decreasing the orientation and apex location diversity between consecutive steps.

ii) The same technique may be applied to the transmit beam and the central receive beam in transmission UDT mode, which are supposed to be collinear.

iii) Similarly, in reflection-based volume imaging, the angular location of a second sub-array's phase center with respect to a first sub-array's phase center may be estimated as follows: the second sub-array should transmit several calibration pulses towards the general direction of the first sub-array. The second sub-array thus "draws a line" over the image acquired by the first sub-array, which can be detected and directionally analyzed.

In further cases, the calibration beams may utilize the assumption that when two beams are aligned, the transmitted and/or reflected signal for the two beams is best matched. Some configurations:

i) In UCT mode, one may switch the roles of the transmitting and the receiving sub-arrays. When the two beams are perfectly aligned, such a switch should have negligible effect on both the overall attenuation and the mean speed of sound measured. Some minor mismatch is still expected, mainly due to noise.

ii) The same technique may be applied to the transmit beam and the central receive beam in transmission UDT mode, which are supposed to be collinear.

iii) In reflection-based beam pairs mode, when a pair of beams is precisely aligned, and after flipping one of the datasets, the range-dependent signal for the overlapping portion of the beams should be very similar, since the two sensors are placed on opposite sides of the subject.

The difference between the two datasets is expected to primarily result from differences in cumulative attenuation and time delays along the beams. In order to minimize the effect of these differences when comparing the two datasets, one may also apply local pattern recognition techniques or calculate various functions of local correlation coefficients, rather than simply calculate the overall correlation between pairs of datasets.

In some embodiments, one or more calibration beams can be transmitted when the subject is outfitted with ultrasound garment 110, or upon mode transition. Calibration beams may also be transmitted at certain time intervals during the ongoing operation of various modes, so as to correct for location and/or orientation changes over time.

3) The acquired image data, to which software-based registration techniques may be applied, also providing information regarding the location and/or orientation of multiple sub-arrays or array transducer components. The acquired image data is formed directly in reflection-based volume imaging. Alternatively, acquired image data may be formed in reflection-based beam pairs mode.

In other modes, 2D and/or 3D images are usually generated by reconstruction techniques applied to data acquired by multiple sub-arrays. Such reconstruction techniques may also be utilized in reflection-based beam pairs mode. In these cases, short bursts of reflection-based volume imaging may be used for coordinate system registration. Additionally or alternatively, in UCT or UDT modes, multiple small changes in the orientation and/or location estimate for every sub-array may be introduced prior to reconstruction, and the configuration providing the sharpest overall image should be selected.

In certain embodiments, transducer components having a very high reflection coefficient ("strong reflectors") may be embedded in known positions along ultrasound garment 110. Different strong reflectors may have different shapes or different reflection characteristics, so as to allow discrimination between them. In reflection-based modes, strong reflectors should be well visible in the obtained image, assuming the coverage volume includes ultrasound garment 110's surface. Such strong reflectors thus provide additional information concerning the relative position and/or orientation of various transmitting and/or receiving transducer components or sub-arrays.

In some embodiments, data provided by two or more of the abovementioned sources is combined or fused. Data fusion may be performed using any technique known in the art. For example, if a sensor array is present and/or calibration beams are transmitted, their measurements may be used to initialize a software-based registration process. Additionally or alternatively, linear or non-linear combinations of the different estimates can be used. For instance, the final estimated location and/or orientation may be set to the software solution if the difference between the two estimates is lower than a predefined value. Otherwise, the final estimated location and/or orientation would be set to the sensor array (and/or calibration beam) measurement.

Software-Based Registration

As mentioned hereinabove, the image in UCT and UDT modes is reconstructed using multiple sub-arrays. Therefore, this subsection relates especially to the fundamental reflection modes.

Software-based registration methods may be coarsely divided into two groups—rigid registration and elastic registration. Rigid registration assumes that the two or more datasets registered describe a rigid body, so that only global translation and rotation of the datasets are required; for example as taught in U.S. Pat. No. 6,159,152; Dec. 12, 2000, by Sumanaweera T S, Pang L, Bolorforosh S S; "Medical Diagnostic Ultrasound System and Method for Multiple Image Registration". Elastic registration also allows for local deformation, for example due to soft tissue deformation, in motion of subject 102 or organ motion, as described by Krücker J F, LeCarpentier G L, Fowlkes J B, Carson P L; "Rapid Elastic Image Registration for 3-D Ultrasound"; IEEE Transactions on Medical Imaging 2002; 21: 1384-1394.

Each process may utilize one or more similarity measures, for example, mutual information measures, correlation coefficient on intensity values or on gradient images, and intensity values using optic flow hypothesis. In some cases, the registration accuracy may be better than the spatial resolution, in which case it is referred to as "sub-pixel resolution" registration. Within this document, the term "pixel" relates to picture transducer components of 1D, 2D, and 3D datasets. The term "voxel", sometimes referring to 3D picture transducer components, is not used.

In the fundamental reflection modes, for each frame (or time-frame), the datasets registered are obtained approximately at the same time. Consequently, one may assume that the 1D, 2D, or 3D images describe certain regions of a large rigid volume, and thus apply rigid registration techniques, using, for example, sub-pixel resolution.

However, since the speed of sound changes from one medium to the other, the time difference between the pulse generation and the arrival of the reflected signal, which is used to estimate the reflector's distance from the US transducer array 110 or sub-array, also depends on the tissue types along the beam path; and therefore on the beam path itself. Elastic registration techniques can therefore provide more accurate or additional information. In some cases, a single registration step may be applied, which is either rigid or elastic. In other cases, two registration steps may be used: rigid registration, followed by elastic registration, which improves overall performance, and can also provide an input to further data extraction processes.

In cases where the target organ moves significantly during data acquisition, the dataset acquired should be time dependent, and temporal registration should also be employed, for example using electrocardiography (ECG) gating.

Data Compounding

Data compounding techniques for both reflection-based and transmission-based UCT and UDT modes were mentioned in the "System Modes" section above. The current subsection relates mainly to the fundamental reflection modes.

Fundamental Techniques

Once spatially dependent datasets have been obtained by several sub-arrays for a certain time frame, these "input datasets" may be compounded to produce one or more "output datasets", each of which providing information regarding a predefined coordinate grid. These grids can be Cartesian, but other grid types, for example hexagonal, helical, or spherical grids, may also be used. The grid of the output datasets may cover a substantially larger volume than any input dataset grid, thus providing an extended field of view.

A possible compounding method can be based on interpolating the data for each input dataset to the coordinate grid of every output dataset, and then calculating the weighted mean over all input datasets per output grid point; in which case only input datasets whose field of view covers the relevant grid point should be considered.

Alternatively, interpolation may be performed simultaneously to all datasets. Any interpolation technique known in the art can be used for these purposes, for example, linear interpolation, cubic interpolation, and cubic smoothing spline. As a result of such spatial averaging, the output dataset is expected to include lower speckle noise and thermal noise levels. Image contrast may also be improved as a direct result. Furthermore, given sufficient data, accurate information may be ascertained for an output grid in which the distance between adjacent transducer components is smaller than that in the input datasets, so that the resulting spatial resolution would be superior to that in the input datasets.

When interpolation is applied separately to each input dataset, the averaging weights may be computed according to various criteria. Some examples:

i. In ultrasound imaging, each sub-array usually produces approximately constant axial (range dependent) resolution, but the lateral (cross-range) resolution may worsen as the distance from the transducer increases. This is a result of using spherical scanning configurations; for example beam steering in azimuth and/or elevation. In addition, when beam steering techniques are used with a constant-size sub-array, the beam width usually increases with the off-broadside angle. Therefore, per output grid point, higher weights can be assigned to input datasets whose near-by pixels provide better lateral resolution. Alternatively, the weights may increase, for example in inverse proportion, as the effective volume of the relevant pixels within an input dataset decreases.

ii. The local SNR per sample in each dataset is a function of various parameters, including, inter alia, the transmission frequency; the distance from the transducer; the beam steering spatial angle; and the cumulative attenuation along the beam, which increases with the distance from the transducer. To obtain optimal results, the averaging weights can also depend on the local SNR estimate per dataset.

iii. In some cases, highly absorbent or reflective regions within a sub-array's coverage area may cause shadowing in the image, i.e., substantially reduce the signal levels received from scanned regions located behind them along the relevant ultrasound beams. In order to cope with this effect, low weights may be assigned to datasets in which the local signal level is significantly lower than in the other datasets. A variety of operators may be applied for this purpose. For example, the signal level may be compared to the local arithmetic or geometric average over all datasets, the median over all datasets, a certain percentile of the datasets, or the average over all datasets plus a certain multiple of the standard deviation over all datasets.

Overall performance may be enhanced by the following iterative process:

i. Calculate an output dataset, according to the methods described hereinabove.

ii. Interpolate the output dataset in order to estimate the values for every grid point of each input dataset.

iii. Compare the results to the input datasets, and update the output dataset accordingly. For example, very large differences between an input dataset and an interpolated output dataset may be detected, following a local update of that region within the output dataset.

iv. If certain cessation criteria, for example maximal number of iterations, or negligible changes in the output dataset over the last iteration, have not been met, return to step ii.

Multi-Frequency Datasets

As mentioned before, multiple sub-arrays may transmit simultaneously or approximately simultaneously, using orthogonal or almost orthogonal waveforms. Scanning each small region within a target volume by multiple transmission frequencies or waveforms may also be used to extract additional or improved information.

One aspect of this matter relates to the fact that, for a given sub-array configuration, the beam pattern changes with the transmission waveform. Therefore, highly reflective transducer components in the beam side-lobes, causing side-lobe clutter (also discussed below), contribute differently to the samples in different waveforms. Averaging or weighted averaging over datasets of several different waveforms can thus reduce clutter effects.

Another aspect is tissue classification. For each grid point of an output dataset, various functions of the adjacent input dataset grid points of different waveforms can be calculated, providing information regarding tissue type. For example, statistical attributes of the waveform dependent data, such as standard deviation or maximum to minimum ratio, can be utilized.

Inaccuracies in the time-gain control (TGC) process, applied prior to data compounding, may introduce errors into the measurements for one or more waveforms, and consequently skew the tissue classification results.

Attenuation Correction

Signal attenuation in ultrasound imaging is usually described in terms of a local attenuation coefficient $\lambda(r,\theta,\phi)$ (r, $\theta$ and $\phi$ are the three spherical coordinates), whose effect on reflected echo measurement is cumulative in logarithmic units. The effective one-way (transmit or receive) energy attenuation factor for a distance R along a beam whose boresight points at a spatial angle $(\theta,\phi)$, is given by:

$$\exp\left[-\int_0^R \lambda(r, \theta, \phi) dr\right].$$

When the signal energy is given in logarithmic units, for example in decibels, the effective one-way energy attenuation factor is $$-\int_0^R \lambda(r, \theta, \phi) dr.$$

The integral is often replaced by summation over discrete values.

A local attenuation coefficient map may be derived from the outputs of the transmission-based UCT mode. By activating both this UCT mode and a reflection-based mode at a certain sequence, for example at interleaving frames, one may use the UCT-based attenuation map to correct the reflection-based map. However, this process increases the data acquisition duration per frame, and thus increases system sensitivity to motion of the subject and/or the imaged organ.

In some embodiments of the invention, local attenuation measurements, which provide important spatially and/or temporally dependent clinical information, and allow improving ultrasound images by applying local attenuation correction, may be performed using only reflection-based information. The following is an explanation of just one method for providing local attenuation measurements for an ultrasound garment of the present invention; as well as existing ultrasound imaging systems. The main concept underlying this method is that elastic registration between multiple input datasets can provide multiple logarithmic energy measurements $m_q$ (q is the dataset index) for each small target region, located in all input datasets by registration. Each of these measurements $m_q$ undergoes cumulative attenuation along a different path $\vec{r}_q$. Data acquisition geometry is generally known, so that a set of equations may be written, describing the relationships between $\lambda(r,\theta,\phi)$ values for different regions. For example, for a single small target region, viewed by two paths $\vec{r}_{q1}$ and $\vec{r}_{q2}$:

$$\int_{\vec{r}_{q1}} \lambda(x, y, z) dr - \int_{\vec{r}_{q2}} \lambda(x, y, z) dr = m_{q2} - m_{q1}$$

where (x, y, z) is a Cartesian coordinate system. This equation is referred to as the "two-path attenuation equation".

One possible geometry used for solving this problem is based on pairs of opposite collinear reflection beams, which are also provided by the reflection-based beam pairs mode. First of all, the data for the two beams has to be registered to a single coordinate system with an axial dimension x (ranging between 0 and X), yielding two registered datasets $m_1(x)$ and $m_2(x)$. Since the overall side-to-side attenuation, $\lambda_{tot}$, should be equal in both datasets, it can be easily shown that:

$$m_1(x) = r(x) - \int_0^x \lambda(y) dy$$

$$m_2(x) = r(x) - \int_x^X \lambda(y) dy = r(x) - \lambda_{tot} + \int_0^x \lambda(y) dy$$

$$\Rightarrow r(x) = \frac{1}{2}[m_1(x) + m_2(x) + \lambda_{tot}]$$

$$\int_0^x \lambda(y) dy = \frac{1}{2}[m_2(x) - m_1(x) + \lambda_{tot}]$$

where r(x) is the true reflection coefficient along the axial dimension. These equations, referred to as the "collinear attenuation equations", are only precise for a noise free environment, but are expected to provide acceptable results in real scenarios as well.

In the reflection-based beam pairs mode, elastic registration may be performed either on pairs of opposite collinear beams or on groups of adjacent opposite collinear beams. In the first case, the registration is reduced to a single dimension. As a result, one may look for specific patterns, which should be located in the two beams, for example maxima or minima.

All the located patterns in one beam should be located in the other one as well, as will be explained with respect to FIG. 8.

Figure 8:
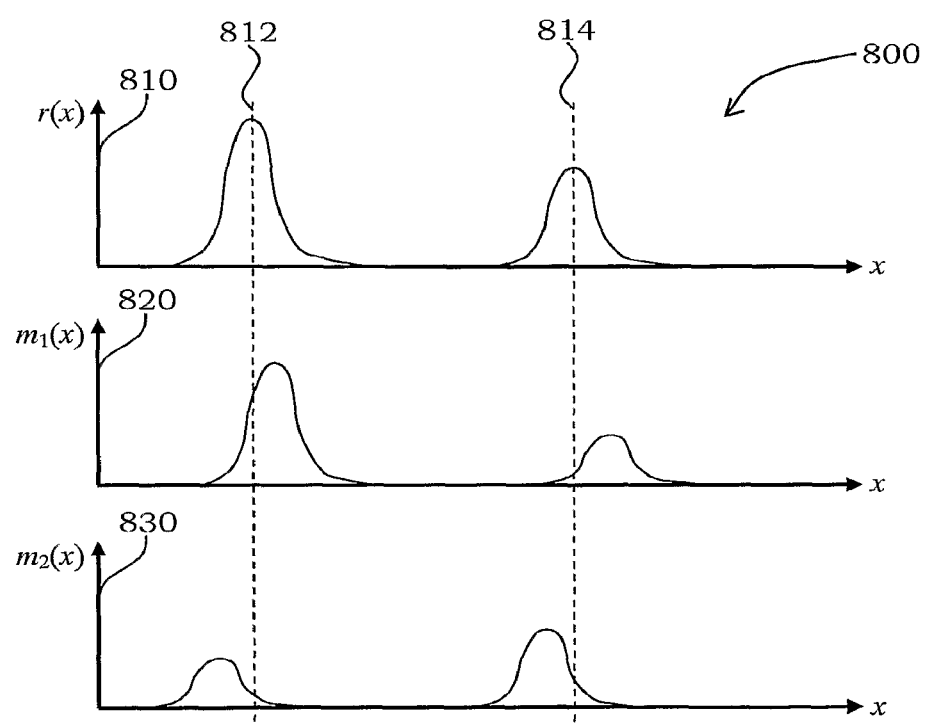
FIG. 8 shows graphs of peak location in collinear beam configurations, according to some embodiments of the invention.

FIG. 8 shows graphs of opposite collinear beams 800 having peaks, as provided by the reflection-based beam pairs mode, including:

a true reflection coefficient graph 810 along the beam;

a left to right reflected signal graph 820, meaning that the reflected ultrasound is measured when looking from left to right; and a right to left reflected signal graph 830, as measured when looking from right to left.

In graph 810, true reflection peak locations are marked by dashed lines 812 and 814. Dashed lines 812 and 814 are extended through left to right reflected signal graph 820 and right to left reflected signal graph 830; in which offsets in peak location are caused by time delays within the tissue with respect to the nominal speed of sound, whereas peak level decrease results from cumulative attenuation.

The signal levels at the locations of the peaks or other detected patterns, as determined in the left to right reflected signal and in the right to left reflected signal, may be used to compute the local attenuation coefficient $\lambda(x)$ for various intervals of axial dimension x, using the collinear attenuation equations. One can assume that the attenuation coefficient $\lambda(x)$ is homogeneously spread over regions between adjacent detected peaks or other patterns. This computation may be repeated for multiple beam pairs, thus providing an attenuation coefficient map for a 2D or 3D region.

This process is only applicable if full side-to-side information has been obtained for all applicable beam pairs. In other cases, one can generate an attenuation coefficient map for all volumes covered by beam pairs with full side-to-side coverage, and then iteratively use this map to complete missing information in beams with partial coverage.

In another embodiment, the output dataset grid may be divided into layers taken at incremental ranges. The layers may take any shape, for example parallel Cartesian layers or dome shaped layers about a predefined reference point (using spherical coordinates).

A set of equations similar to the two-path attenuation equation is optionally written for all output grid points within each layer, assuming that the attenuation values for the output grid points in all layers closer to the reference point, have already been determined. For the first layer, the attenuation within the entire previous layer is assumed to be 0 [dB]. This "boundary condition" allows the solution of the equations for all layers.

The above described processes results in an estimated map of attenuation coefficients, which is spatially dependent, and in some cases also time dependent. This map may also be used to correct the map of reflection coefficients, inherently produced by reflection-based imaging modes. Combining the two maps, perhaps together with other maps provided by the system, can aid in the classification of tissue types. Additionally or alternatively, the complex weights assigned to different transducers 124 on transmit and/or on receive may be adjusted for each small scanned volume based on the attenuation coefficient maps, for example in order to improve focusing on transmit and/or on receive, thus enhancing spatial resolution.

The above procedures may take into account the spatially dependent gain, for example due to time-gain control (TGC), applied prior to the procedures by the system hardware and software. For that purpose, a local TGC correction factor may be added to the attenuation coefficient map obtained, and/or to the samples used as an input to the process.

In some cases, various additional corrections may be applied to the sampled data and/or the energy measurements prior to the attenuation correction process. For example, one may choose to correct for the two-way range dependent power decay of the spherical ultrasound wave, which approximately follows the form $1/R^4$ (where R is the distance from the transducer). Additionally or alternatively, one can compensate for beam-shape losses, caused by the fact the energy of the transmit beam and the gain of the receive beam are not homogeneously distributed over all spatial angels, or even over all spatial angles within the respective main-lobes.

The tissue's local attenuation coefficient may depend on the transmitted frequency. Therefore, when wideband signals are transmitted, the process described above may be applied separately to multiple sub-bands of the received signal. The results for the multiple sub-bands may then be combined to obtain the final attenuation coefficient estimation. The received signal may be divided into sub-bands by applying analog and/or digital filtering to that signal. In some cases, different sub-bands may also be sampled separately.

Corrections for Speed of Sound Variability

The average speed of sound in soft tissue is approximately 1540 [m/sec]. However, this speed varies between different tissue types. During reflection-based image formation, one often assumes a constant speed of sound, so that the time delay between signal transmission and the receipt of the reflected signal is linearly correlated to the distance from the transducer. Variations in speed of sound introduce positive or negative time delays, making this correlation imprecise.

The actual local speed of sound may be estimated using the transmission-based UCT mode. This mode can therefore be activated in some sequences with a reflection-based mode, for example interleaving frames, and its output may be used to correct the reflection-based map.

In some embodiments of the invention, local speed of sound measurements, which provide important spatially and/or temporally dependent clinical information and allow improving ultrasound images by applying local time delay correction, may be performed using only reflection-based information. The following is an explanation of just one method for providing local attenuation measurements for an ultrasound garment of the present invention; as well as existing ultrasound imaging systems. This method is based on the fact that elastic registration between multiple input datasets can provide multiple translation measurement $\vec{t}_q$ (q is the dataset index) for each small target region with respect to a selected reference input dataset. These translations are indicative of relative time delays. As with signal attenuation, signal time delay is also cumulative along each beam path $\vec{r}_q$. Data acquisition geometry is generally known, so that a set of equations may be written, describing the relationships between $\vec{t}_q$ values for different regions. For example, for a single small target region, viewed by two paths $\vec{r}_{q1}$ and $\vec{r}_{q2}$:

$$\int_{\vec{r}_{q1}} \frac{2 dr}{c(x,y)} - \int_{\vec{r}_{q2}} \frac{2 dr}{c(x,y)} = t_{q1} - t_{q2}$$

where c(x,y) is the actual local speed of sound, $t_{q1}$ and $t_{q2}$ are the scalar time delays along paths $\vec{r}_{q1}$ and $\vec{r}_{q2}$ respectively. This equation is referred to as the "two-path time-delay equation".

A possible geometry used for solving this problem is based on pairs of opposite collinear reflection beams, which can be provided by the reflection-based beam pairs mode. For each set of beam pairs, one should look for specific patterns, for example maxima or minima. All the located patterns in one beam should be located in the other one as well (FIG. 8). The actual location of the peaks, or other patterns, along the beam pairs axis is denoted by l(x), and the measured locations along the two opposite beams are $l_1(x)$ and $l_2(x)$. The local time delay, given in units of range, is denoted by d(x). Since the overall side-to-side time delay, D, should be equal in both datasets, it can be easily shown that:

$$l_1(x) = l(x) + \int_0^x d(y) dy$$

$$l_2(x) = l(x) + \int_x^X d(y) dy = l(x) + D - \int_0^x d(y) dy$$

$$\Rightarrow l(x) = \frac{1}{2}[l_1(x) + l_2(x) - D]$$

$$\int_0^x d(y) dy = \frac{1}{2}[l_1(x) - l_2(x) + D]$$

The local speed of sound can be directly extracted from these equations, referred to as the "collinear time-delay equations", as the time delay is proportional to the difference between the actual speed of sound and the nominal speed of sound. While these equations may only be precise for a noise free environment, they should provide acceptable results in real scenarios as well.

The collinear time-delay equations provide measurements of the local time delay for the locations of the peaks or other patterns detected. One can assume that the time delay is homogeneously spread over regions between adjacent detected peaks (or other patterns). This computation may be repeated for multiple beam pairs, thus providing a speed of sound map for a 2D or 3D region.

This process is only applicable if full side-to-side information has been obtained for all beam pairs. In other cases, one can generate a speed of sound map for all volumes covered by beam pairs with full side-to-side coverage, and then use this map to iteratively complete missing information in beams with partial coverage.

In a further embodiment, applicable for example to reflection-based volume imaging, the output dataset grid may be divided into layers taken at incremental ranges. The layers may take any shape, for example parallel Cartesian layers, or dome shaped layers about a predefined reference point (using spherical coordinates).

A set of equations is optionally written for all output grid points within each layer, assuming that the speeds of sound for the output grid points in all layers closer to the reference point have already been determined. For the first layer, the speed of sound in the previous layer is assumed to be the nominal speed of sound. This "boundary condition" allows the solution of the equations for all layers.

The resulting spatial map of speeds of sound, which in some cases can also be time dependent, may be used to correct the reflection coefficient map, inherently produced by reflection-based imaging modes. It can also be used separately. Moreover, combining the two maps, perhaps together with other maps provided by the system, can aid in the classification of tissue types. Additionally or alternatively, the complex weights assigned to different transducers 124 on transmit and/or on receive may be adjusted for each small scanned volume based on the speed of sound maps, for example in order to improve focusing on transmit and/or on receive, thus enhancing spatial resolution.

The local speed of sound within the tissue may depend on the transmitted frequency. Therefore, when wideband signals are transmitted, the process described above may be applied separately to multiple sub-bands of the received signal. The results for the multiple sub-bands may then be combined to obtain the final speed of sound estimation. The received signal may be divided into sub-bands by applying analog and/or digital filtering to that signal. In some cases, different sub-bands may also be sampled separately.

Side-Lobe Clutter Suppression Techniques

The term "clutter" refers to undesired information that appears in the imaging plane, obstructing the data of interest. One of the most common reasons for clutter in ultrasound images is effective imaging of off-axis objects, lying in a beam's side-lobes. Highly reflective regions within these side-lobes, for example surfaces between soft and hard tissues, may produce significant contributions to the measured signal.

An iterative process may be devised to minimize clutter effects:

1) Acquire one or more frames of data for the target volume, using, for example, an ultrasound garment 110-based system.
2) For each sample (range gate) at each beam position:
   i) Calculate the beam pattern for the current range, with respect to the applicable scanning apex, at all other beam positions, normalized so that the peak value would be 1.0.
   ii) For complex measurements—subtract from the sample the value at the same range, with respect to the applicable scanning apex, for all other beam positions, multiplying each value by the relevant normalized beam pattern value. Alternatively, only beam positions for which the measurement and/or the normalized beam pattern value is high are used. The criterion for selecting the beam positions used for a certain range gate may be, for example, that the measurement and/or the normalized beam pattern value and/or their multiplication result exceeds a certain threshold or belongs to the group of B highest values, where B is a constant. The second method is also applicable to real measurements.
   iii) Repeat step ii until certain cessation criteria have been met. This is required because all measurements are affected by reflectors in all beam positions, so that there are interdependencies between the samples. The cessation criteria may be as simple as reaching a certain number of iterations. More complicated criteria may refer to the average magnitude of changes made in the last iteration, or the relative average magnitude of changes in the last several iterations.

This procedure assumes that the effects of attenuation and variations in the speed of sound are not severe, so that data from different beam positions can be compared. This issue can be avoided by applying attenuation correction techniques and/or time delay corrections prior to clutter suppression.

This process requires that for each processed beam, taken at a spatial angle $(\theta,\phi)$, information would be available for $\theta\pm\Delta\theta$ and $\phi\pm\Delta\phi$, where $\Delta\theta$ and $\Delta\phi$ are high, for example, higher than 30°, or even very high, for example higher than 45°.

The inventor has discovered that some embodiments of present ultrasound probes cannot provide such an angular coverage, but that such angular coverage may possibly be achieved in ultrasound garment 110-based systems. Data acquired by more than one sub-array may result in different attenuation models for different sub-arrays. The effect of these differences may be mitigated by applying attenuation correction schemes, such as those described hereinabove.

Computer Aided Diagnosis Techniques

Diverse computer aided diagnostic tools may be developed in order to streamline the diagnostic process and make it quantitative rather than qualitative. Some clinical applications may also require organ specific tools. For instance, a software tool may be developed which automatically detects the fetal skin surface, delineating it from the amniotic fluid. Based on this surface, various standard imaging views, for example the sagittal or coronal view of the brain, may be automatically defined by the software and displayed to the operator. Another example is a tool designed for evaluating fissure complexity within the fetal brain.

Additional System Modes

Doppler Mode

The Doppler effect is the most common tool for measuring blood flow velocities and tissue motion velocities in standard ultrasound imaging systems. For reflection-based ultrasonic imaging, this effect is described by the following equation:

$$f_D = \frac{2fv\cos(\theta)}{c}$$

where f is the transmitted frequency; v is the absolute flow (or motion) velocity; $\theta$ is the angle between the effective directions of the ultrasonic beam and the flow (or motion) velocity; c is the wave speed; and $f_D$ is the Doppler shift, i.e., the difference between the frequencies of the observed and the transmitted ultrasound. $v\cos(\theta)$ is the radial velocity component, i.e., the velocity's component along the line of sight from the transducer's phase center to the target, so that the Doppler shift is directly proportional to the radial velocity.

Five types of Doppler modes are usually supported by ultrasound systems:
   i. CW Doppler studies, which provide the overall radial velocity spectrum for a specific beam direction. The output usually takes the form of a two-dimensional graph, where the horizontal axis is the time index and the vertical axis is the radial velocity, which may either be positive or negative. The gray-level of each pixel denotes the local ratio, along a selected direction, between the number of particles moving at the relevant radial velocity and the total number of particles. Thus, the outlines of the graph show the maximal velocity as a function of time.
   ii. PW Doppler studies, which provide the radial velocity spectrum for a selected depth along a specific angular direction, as a function of time. The display method is identical to that used in CW Doppler studies.
   iii. Color flow Doppler imaging, which uses PW, superimposes a color representation of the dominant radial blood flow velocity (for each pixel) over a 2D or 3D ultrasonic image, which may or may not be time dependent.
   iv. Tissue Doppler imaging can assess the radial tissue motion velocity in vascular and cardiac imaging using PW. As in color flow Doppler imaging, the information is superimposed over the ultrasonic image.
   v. Power Doppler imaging, which is similar to color flow Doppler and tissue Doppler imaging. It displays for each pixel the signal energy for the local dominant Doppler shift. The signal energy is proportional to the number of particles within the pixel volume which move at the dominant radial velocity.

Both CW Doppler studies and PW Doppler studies may be used to measure either blood flow velocity, for example through a valve or a blood vessel, or muscle/valve motion velocity, whose peaks are normally at much lower velocities.

All the above Doppler modes can be supported by an ultrasound garment 110-based system. Additional benefits may also be obtained by the use of multiple sub-arrays. Some applications:
   i. In PW Doppler studies, a full spectrum for a specific region may be acquired from multiple directions, thus extending the information provided to the clinician.
   ii. In CW Doppler studies, which provide range independent information for a specific direction, one may use two or more intersecting beams, whose boresight directions may either be constant or changing over time, to extract spatially dependent data. For example, two beams may be used, the first pointing in a specific direction, whereas the second one scans the path of the first beam. If an exceptionally low or an exceptionally high value is found along the first beam, and is found again, not necessarily with the same value, for a specific direction of the second beam, one can assume that the extreme value corresponds to the intersection point between the first and second beam.
   iii. In color flow Doppler and tissue Doppler imaging, one can scan a certain volume using two or more sub-arrays, either on receive only, or both on transmit and on receive. Two or more points of view may be used to reconstruct for each pixel a 2D projection of the 3D velocity vector corresponding to the dominant velocity. Three or more points of view may be used to reconstruct the full 3D velocity vector for each pixel. This can be performed as follows: The radial velocity measurement for the i'th point of view, $v_i^r$, as made using a beam whose boresight unit vector is $\hat{b}_i=(x_i,y_i,z_i)$, provides the projection of the local dominant velocity vector $\vec{v}=(v_x,v_y,v_z)$ on $\hat{b}_i$, i.e., $\hat{b}_i \cdot \vec{v}$. All unit vectors $\hat{b}_i$ are known, so that the vector $\vec{v}$ may be deduced from three measurements:

$$\begin{pmatrix} v_1^r \\ v_2^r \\ v_3^r \end{pmatrix} = \begin{pmatrix} x_1 & y_1 & z_1 \\ x_2 & y_2 & z_2 \\ x_3 & y_3 & z_3 \end{pmatrix} \begin{pmatrix} v_x \\ v_y \\ v_z \end{pmatrix} \Rightarrow \begin{pmatrix} v_x \\ v_y \\ v_z \end{pmatrix} = \begin{pmatrix} x_1 & y_1 & z_1 \\ x_2 & y_2 & z_2 \\ x_3 & y_3 & z_3 \end{pmatrix}^{-1} \begin{pmatrix} v_1^r \\ v_2^r \\ v_3^r \end{pmatrix}$$

where $-1$ denotes a matrix inversion operator. A similar process can be applied to obtain only a 2D projection of the vector.

Using more points of view than needed allows obtaining a vector estimate for each group of two or three points of view. Averaging over the results may provide more accurate results.

In some cases, one can limit the volume scanned for Doppler processing to a specific region, which is either operator defined or automatically selected. The specific region can be defined based on anatomic maps, for example by locating blood vessels of interest and their immediate surroundings. By limiting the scanned is volume, the number of beam positions required to scan the volume is decreased, so that the overall refresh rate can be increased. This is important when significant changes are expected over time, for example in cardiac imaging.

Moving-Organ Tissue Tracking

Some organs, for example blood vessels, the cardiac muscle, and the gastrointestinal system, move over time. One can evaluate this motion in ultrasound imaging by tracking small localized regions of the image between consecutive image frames; for example as described by Ledesma-Carbayo M J, Kybic J, Desco M, et al.; "Spatio-Temporal Non-rigid Registration for Ultrasound Cardiac Motion Estimation"; IEEE Transactions on Medical Imaging 2005; 24:1113-1126. This can be done by applying various elastic registration techniques, for example by optic flow methods, to datasets obtained at subsequent time frames.

Such schemes may be utilized by ultrasound garment 110-based systems. For example, they may be applied to datasets obtained by one or more sub-arrays and/or to compounded datasets, produced by any imaging mode. The resulting information can be provided to the operator.

Contrast Imaging

Several contrast ultrasound imaging methods are known in the art. In some cases, these methods are tailored to a specific organ. All these methods are also applicable to ultrasound garment 110-based systems.

Elastography

In some embodiments, ultrasound garment 110-based systems may provide elastography features. Any type of internal or external mechanical stimulus, generated by any source, may be used for that purpose. For example, a stimulus may be generated by one or more loudspeakers, one or more transducers 124, and/or one or more apparatuses comprising a housing with a movable surface, as taught in US Patent Application 2002/0068870; Jun. 6, 2002 by Alam S K, Feleppa E J, King M, Lizzi F L; "Hand Held Mechanical Compression Device for Inducing Tissue Strain".

The vibration frequency of the source optionally will vary between 1 [Hz] and 100 [kHz].

The inventor has discovered that the use of multiple sources may allow producing more localized excitation by means of interference, as well as improving the control over the directionality of the mechanical impulse generated.

Another method for creating a mechanical stimulus, is applying a constant or time-variable force to the subject's skin surface, or to an internal organ, during invasive procedures. While a mechanical force is being applied, either in a cyclic fashion (vibration) or in a non-cyclic fashion, tissue tracking techniques, for example as described by in the "Moving Organ Tissue Tracking" subsection, may be applied, producing estimates of the local tissue motion vectors in response to the mechanical force. Additionally or alternatively, Doppler-based imaging modes, as described herein, may be used to estimate the local time-dependent motion vectors of the tissue. These vectors are indicative of the tissues' mechanical properties, and may be used for tissue classification purposes, for example detection of malignant or benign tumors.

In a possible configuration, one or more low-frequency sound sources (LFSSs), such as loudspeakers, are placed either in direct contact with, or in close proximity to, the subject's skin surface. These LFSSs, which can be integrated with an ultrasound garment 110-based system or placed near it, produce directional oscillations within the imaging target volume. In this configuration, the LFSS carrier frequency should optionally be lower, by a factor of at least 5, than the highest pulse repetition frequency used by any sub-array of ultrasound garment 110 system during the elastography mode. This can aid in preventing smearing of the measured signal, for example, so as to assure that local tissue motion during the pulse is insignificant.

The LFSS carrier frequency is typically selected to be low enough to produce negligible tissue motion during the acquisition of a full imaging frame, or at least a large sector of such a frame, so that images can be obtained at multiple phases of a single LFSS oscillation. If that is not the case, the temporal sampling for each small tissue region is unsynchronized with the LFSS oscillation, so that one may only be able to estimate the span or extent of the local tissue motion over multiple cycles rather than determine the time dependent motion pattern.

Photoacoustic and Thermoacoustic Imaging

Photoacoustic imaging is a medical imaging modality based on the photoacoustic effect. Non-ionizing laser pulses are delivered into biological tissues; some of the delivered energy is converted into heat, leading to transient thermoelastic expansion and thus ultrasonic emission. The generated ultrasonic waves are then detected by ultrasonic transducers to form images. The energy of the ultrasonic emission is indicative of the local energy deposition, and therefore provides information regarding the local optical absorption. The energy of the ultrasonic signals received by the ultrasonic transducers is also affected by two types of artifacts:

i. Electromagnetic phenomena, occurring along the path of the electromagnetic signal.
ii. Ultrasonic phenomena, occurring along the ultrasound propagation path.

These phenomena include, for example, absorption, reflection, and scattering.

An exemplary photoacoustic imaging system is described by Zhang H F et al.; "Functional Photoacoustic Microscopy for High-Resolution and Noninvasive In-vivo Imaging"; Nature Biotechnology 2006; 24:848-851.

When radio-frequency (RF) pulses are used, the technology is referred to as thermoacoustic imaging rather than photoacoustic imaging.

Optical absorption and RF absorption are closely associated with physiological properties. For instance, optical absorption is known to be related to local hemoglobin concentration and oxygen saturation. Another exemplary application is visualization of blood vessels, which is based on the fact that both optical absorption and RF absorption of blood tend to be high compared to most other tissue types. Generally speaking, the frequency of the light and/or RF waves used may affect the physiologic properties observed by photoacoustic or thermoacoustic imaging systems, as well as their maximal penetration depth, which tends to increase as the frequency decreases.

The inventor has discovered that ultrasound garments may have application in photoacoustic and thermoacoustic imaging. The following description presents just some of the many possible means of extracting information to provide photoacoustic and thermoacoustic imaging data.

In some embodiments, referring back to FIG. 1, one or more sources of light or RF radiation (jointly referred to hereinbelow as electromagnetic radiation) may be incorporated into ultrasound garment 110-based systems or placed in close proximity to them. The sources of light may include, for example, laser relayed by optic fibers. Lenses may optionally be used to increase the laser beams' coverage area. The RF sources may include any type of RF-fed antenna known in the art, which fits the required transmission power and frequency band, for example, dipole antennas, horn antennas, planar-array antennas, and/or phased-array antennas.

The electromagnetic radiation sources may transmit any waveform, including CW and PW. Optionally, amplitude modulation and/or frequency modulation may be utilized, as well as coded excitation techniques such as binary sequences and poly-phase codes. Different electromagnetic radiation sources may also use different waveforms, thus allowing simultaneous utilization of several electromagnetic radiation sources.

In embodiments, the ultrasound transducers 124 and beamforming unit 120 should optionally be configured to generate one or more concurrent receive beams, whose spatial directions may be constant or time-dependent. The timing of these receive beams may be synchronized to electromagnetic pulse transmission. Since the speed of sound in tissues is lower than the speed of light by several orders of magnitude, the time delay between electromagnetic pulse transmission and ultrasonic signal reception should be approximately proportional to the distance between the tissue from which ultrasound waves emanate and the transducers. Additionally or alternatively, the directions of the receive beams may be adjusted to match the coverage volume of the electromagnetic radiation sources.

Numerous receive beam scanning configurations may be considered. For example, one of more sub-arrays may be defined, each of which scanning a plane or a volume. Additionally or alternatively, a plurality of receive beams may be defined, some of which are parallel and/or directed at a certain point in space. Another option is using pairs of opposite collinear beams.

Processing unit 122 may then apply any reconstruction algorithm known in the art or described herein. In embodiments, reflection mode and/or transmission mode UCT algorithms may be applied, with or without the geometry emulation algorithm. Additionally or alternatively, attenuation correction techniques and/or corrections for speed of sound variability, as described hereinabove, may be utilized in order to minimize the effect of ultrasonic artifacts on local electromagnetic absorption estimates. The calculations may take into account the one-way rather than two-way nature of the ultrasonic artifacts in these cases.

In embodiments, further techniques may be applied to reduce the effect of electromagnetic artifacts occurring between the electromagnetic source and the tissue emitting ultrasound waves. For example, a range-dependent correction factor may be applied. The correction factor may also take into account the ultrasonic signal as measured for tissues along the path between the electromagnetic source and the tissue emitting ultrasound waves.

In further embodiments, additional information may be obtained by transmitting more than one type of electromagnetic waveform, for example more than one transmission frequency.

Additionally or alternatively, where multiple electromagnetic radiation sources are used, the ultrasonic data collected using different electromagnetic radiation sources may be compared and analyzed. For example, when comparing the ultrasonic data along a line connecting two electromagnetic radiation sources, as collected by the two said sources, the collinear time-delay equations may be applied to estimate and optionally correct the electromagnetic time delays within the tissues.

Therapeutic Systems
High Intensity Focused Ultrasound

As described hereinabove, HIFU is an ultrasound-based therapeutic technique. In some embodiments, ultrasound garment 110-based systems can be used as a source of imaging information, guiding an HIFU apparatus. In certain embodiments, this imaging information may also include local temperature estimation at the target region, for controlling HIFU operation. Local temperature may be evaluated based on the multiple parameters measured for each point in space as a function of time, for example local reflection coefficient, local attenuation coefficient, and local speed of sound. In further embodiments, an array of high intensity transducers 124 may be integrated with or into ultrasound garment 110. The radiating transducer components used for HIFU may either be dedicated to HIFU operation or be used for imaging purposes as well.

The inventor has discovered that the local measurements of ultrasound attenuation and/or local speed of sound, made by the processes provided herein, can be used to adaptively optimize the beam forming parameters of the high intensity transducer components. As a result, the focal point can be smaller and more precisely defined, allowing better control over the target region. Additionally or alternatively, lower transmitted power levels may be used to obtain the same effect at the target region, thus improving the system's safety level.

It is expected that during the life of a patent maturing from this application many relevant ultrasound garments will be developed, and the scope of the term ultrasound garment is intended to include all such new technologies a priori.

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques, and procedures by practitioners of the mathematical, physical, chemical, pharmacological, biological, medical, computer sciences, electrical engineering, mechanical engineering, and biomedical engineering arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination, or as suitable in any other described embodiment of the invention. Certain features described in the context of various embodiments are not to be considered essential features of those embodiments, unless the embodiment is inoperative without those components.

In embodiments, some of the algorithms presented herein, such as the geometry emulation algorithm, and/or their combinations or sub-combinations, may be utilized on ultrasound garment embodiments as well as, in some instances, on existing technology.

Ultrasound garment technology may provide some advantages over known imaging modalities. Partial comparative analysis between certain disclosed ultrasound garment configurations and known ultrasound, MRI and CT systems is provided in the following Appendix A; which together with the above descriptions illustrate some embodiments of the invention in a non-limiting fashion.

APPENDIX A

The inventor has discovered the following possible analytical aspects of ultrasound garment systems and presently available ultrasound, MRI and CT systems. ("fps" stands for "frames per second".)

|  | US Garment Systems | Ultrasound | MRI | CT |
|---|---|---|---|---|
| *General Clinical Aspects* | | | | |
| Scanned Volume | May provide a large 3D volume | 2D plane or small 3D volume | Large 3D volume | |
| Clinical Data Accessibility | Possibly any plane or volume within the large 3D volume | Limited by possible transducer locations and tilts | Any plane or volume within the large 3D volume | |
| Refresh Rate | May be high for large 3D volumes | High (~20 fps) for 3D volumes | Low (or still) for large 3D volumes | |
| General Image Quality | Expected to be high | Relatively low | High | |
| Inter- and Intra-Observer Variability | Expected to be low | High | Low | |
| Tissue Classification | Generally supported | Not supported | Not supported | |
| Imaging for Continuous Monitoring | Generally supported | Not supported | Not supported | |
| Exam Location | May be bedside | | Special exam room | |
| Safety | No ionizing radiation | | No ionizing radiation Contrast agents often used | Ionizing radiation |
| *Clinical Aspects Specific to Obstetrics and Gynecology* | | | | |
| Invasive/Non-invasive | May be non-invasive | Trans-abdominal transducers: non-invasive Trans-vaginal transducers: invasive, limited imaging views | Non-invasive | |
| *Additional Clinical Aspects* | | | | |
| Image Quality Dependence on Hardware Configuration | Generally minimal | High | Minimal | |
| Cine-loop Acquisition Duration | May take Several seconds | | Several minutes | |
| Blood Flow Velocity Measurement | 3D flow vectors generally may be measured | Radial component of flow vectors measured | Coarse flow velocity measurements | Not measurable |

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An ultrasound assembly, comprising:
   i. a garment configured to be affixed to a portion of a living body;
   ii. at least one ultrasound transducer having a fixed position on said garment and configured to provide at least one of:
      a) produce; and
      b) receive ultrasound signals that pass through the living body;
   iii. an ultrasound processing unit operatively associated with said at least one ultrasound transducer and configured to process said ultrasound signals following passage through the living body; and
   iv. an ultrasound operator-interface unit operatively associated with said ultrasound processing unit and configured to provide information with respect to said ultrasound signals following passage through the living body, wherein said at least one transducer comprises at least one transducer array;
   including an ultrasound beam-forming unit configured to produce ultrasound beam propagation wherein at least one of:
      i. at least one sub-array;
      ii. said at least one array;
      iii. a plurality of transducer arrays; and
      iv. said at least one transducer are configured to provide beams consisting of at least one of:
         a. transmitting; and
         b. receiving, and
   said ultrasound processing unit includes a software module configured to process information from said provided beams, wherein said system includes at least one of:
      i. a plurality of sub-arrays; and
      ii. said plurality of transducer arrays, and wherein said ultrasound processing unit includes a software module configured to compound signals received to produce at least one output dataset.

2. The assembly according to claim 1, including at least one rail juxtaposed along said garment and at least one of:
   i. at least one sub-array;
   ii. said at least one array;
   iii. a plurality of transducer arrays; and
   iv. said at least one transducer, are configured to move along said at least one rail.

3. The assembly according to claim 1, including at least one transducer-locating sensor operatively associated with said ultrasound processing unit, said at least one transducer-locating sensor occupying at least one position of:
   i. on said garment; and
   ii. at a distance from said garment, and
   said ultrasound processing unit includes a second software module configured to process spatial information from said at least one transducer-locating sensor.

4. The assembly according to claim 1, wherein said at least one dataset comprises at least two data sets which are combined, thereby achieving at least one of:
   i. extending a field of view;
   ii. reducing speckle noise;
   iii. improving signal-to-noise ratio;
   iv. reducing shadowing artifacts;
   v. reducing clutter artifacts;
   vi. enhancing spatial resolution; and
   vii. enhancing image contrast.

5. The assembly according to claim 1, wherein the software module is configured to produce output datasets from input datasets; wherein said input datasets comprise information from said provided beams; by:
   i. interpolating data for each input dataset to a coordinate grid of every output dataset;
   ii. calculating a weighted mean over all input datasets per output grid point, using input data sets whose field of view covers the relevant grid point.

6. The assembly according to claim 5, wherein the weights for said weighted mean may be computed according to various criteria, said various criteria comprising at least one of:
   i. higher weights are assigned to input datasets whose nearby pixels provide better lateral resolution;
   ii. weights are assigned in inverse proportion to the effective volume of the relevant pixels within an input dataset;
   iii. weights are assigned according to a signal-to-noise ratio estimate per input dataset; and
   iv. low weights are assigned to datasets in which the local signal level is significantly lower than in the other datasets.

7. The assembly according to claim 1, including at least one transducer, producing different waveforms, wherein said ultrasound processing unit includes a second software module configured to provide various functions of datasets acquired by said at least one transducer at different waveforms that are calculated, thereby providing information with respect to local tissue type.

8. The assembly according to claim 1, wherein said ultrasound beam-forming unit is configured to support at least one imaging mode comprising at least one of:
   i. reflection-based volume imaging;
   ii. reflection-based ultrasound computed tomography (UCT);
   iii. reflection-based ultrasound diffraction tomography (UDT);
   iv. reflection-based beam pairs;
   v. transmission-based UCT; and
   vi. transmission-based UDT.

9. The assembly according to claim 1, wherein said ultrasound processing unit includes a second software module configured to receive data from calibration beams, wherein said calibration beams include at least one of:
   i. transmit beams; and
   ii. receive beams, and
   said second software module aligns said transmit beams and said receive beams.

10. The assembly according to claim 1, wherein multiple strong reflectors are embedded in known positions along said garment; said strong reflectors comprising at least one of:
    i. different shapes; and
    ii. different reflection characteristics, and
    said ultrasound processing unit includes a second software module configured to discriminate between said strong reflectors.

11. The assembly according to claim 1, wherein an array of high intensity transducers is integrated into said ultrasound garment and at least one said high intensity transducer is at least one of:
    i. dedicated to high intensity focused ultrasound (HIFU) operation; and
    ii. dedicated to imaging purposes, and
    wherein said ultrasound processing unit includes a second software module configured to utilize at least one of:
    i. the local measurements of ultrasound attenuation; and
    ii. the local measurements of speed of sound, to adaptively optimize the beam-forming parameters of said high intensity transducers.

12. The assembly according to claim 1, wherein said garment comprises at least one apparel comprising at least one of:
    a belt;
    a shirt; and
    a pair of pants.

13. An ultrasound assembly, comprising:
    i. a garment configured to be affixed to a portion of a living body;
    ii. at least one ultrasound transducer having a fixed position on said garment and configured to provide at least one of:
       a) produce; and
       b) receive ultrasound signals that pass through the living body;
    iii. an ultrasound processing unit operatively associated with said at least one ultrasound transducer and configured to process said ultrasound signals following passage through the living body; and
    iv. an ultrasound operator-interface unit operatively associated with said ultrasound processing unit and configured to provide information with respect to said ultrasound signals following passage through the living body, wherein said at least one transducer comprises at least one transducer array;
    including an ultrasound beam-forming unit configured to produce ultrasound beam propagation wherein at least one of:
    i. at least one sub-array;
    ii. said at least one array;
    iii. a plurality of transducer arrays; and
    iv. said at least one transducer are configured to provide beams consisting of at least one of:
       a. transmitting; and
       b. receiving, and
    said ultrasound processing unit includes a software module configured to process information from said provided beams, wherein said ultrasound processing unit is configured to receive input datasets acquired from multiple directions, and, for at least one small target region located in more than one of said input datasets, apply an elastic registration process to relevant measurements in said input datasets.

14. The assembly according to claim 13, wherein said ultrasound processing unit extracts from outputs of said elastic registration process at least one of:
   i. local attenuation coefficient measurements; wherein said elastic registration process is applied to at least two of said input data sets undergoing cumulative attenuation along different paths; wherein said cumulative attenuation results from local attenuation within said living body; and
   ii. local speed of sound measurements;
   wherein said elastic registration process is applied to at least two of said input data sets undergoing cumulative time delays along different paths;
   wherein said cumulative time delays result from local attenuation within said living body.

15. An ultrasound assembly, comprising:
   i. a garment configured to be affixed to a portion of a living body;
   ii. at least one ultrasound transducer having a fixed position on said garment and configured to provide at least one of:
      a) produce; and
      b) receive ultrasound signals that pass through the living body;
   iii. an ultrasound processing unit operatively associated with said at least one ultrasound transducer and configured to process said ultrasound signals following passage through the living body; and
   iv. an ultrasound operator-interface unit operatively associated with said ultrasound processing unit and configured to provide information with respect to said ultrasound signals following passage through the living body, wherein said at least one transducer comprises at least one transducer array;
   including an ultrasound beam-forming unit configured to produce ultrasound beam propagation wherein at least one of:
      i. at least one sub-array;
      ii. said at least one array;
      iii. a plurality of transducer arrays; and
      iv. said at least one transducer are configured to provide beams consisting of at least one of:
         a. transmitting; and
         b. receiving, and
   said ultrasound processing unit includes a software module configured to process information from said provided beams, wherein said ultrasound processing unit includes a software module based process configured to reduce clutter effects by carrying out an operation, comprising:
      i. acquiring at least one frame of data for the target volume; and
      ii. for each sample range-gate at each beam position calculating a beam pattern for the current range, with respect to an applicable scanning apex, at all other beam positions;
   wherein said beam pattern is normalized so that the peak value is 1.0.

16. The assembly according to claim 15, wherein said software module-based process is further configured to subtract from said sample range-gate measurement values at the same range, with respect to said applicable scanning apex, for a group of other beam positions, where each measurement value is multiplied by the corresponding said beam pattern value, and wherein said group of other beam positions comprises beam positions for which at least one value is high, said high value comprising at least one of:
   i. a measurement; and
   ii. said beam pattern.

17. An ultrasound assembly, comprising:
   i. a garment configured to be affixed to a portion of a living body;
   ii. at least one ultrasound transducer having a fixed position on said garment and configured to provide at least one of:
      a) produce; and
      b) receive ultrasound signals that pass through the living body;
   iii. an ultrasound processing unit operatively associated with said at least one ultrasound transducer and configured to process said ultrasound signals following passage through the living body; and
   iv. an ultrasound operator-interface unit operatively associated with said ultrasound processing unit and configured to provide information with respect to said ultrasound signals following passage through the living body, wherein said at least one transducer comprises at least one transducer array;
   including an ultrasound beam-forming unit configured to produce ultrasound beam propagation wherein at least one of:
      i. at least one sub-array;
      ii. said at least one array;
      iii. a plurality of transducer arrays; and
      iv. said at least one transducer are configured to provide beams consisting of at least one of:
         a. transmitting; and
         b. receiving, and
   said ultrasound processing unit includes a software module configured to process information from said provided beams, wherein said ultrasound processing unit includes a software module configured to generate ultrasound computed tomography or ultrasound diffraction tomography images by geometrically transforming at least one of:
      i. scanning processing parameters; and
      ii. signal processing parameters; to obtain samples equivalent to those obtained using at least one of:
         a. cylindrical geometry; and
         b. spherical geometry.

18. An ultrasound assembly, comprising:
   i. a garment configured to be affixed to a portion of a living body;
   ii. at least one ultrasound transducer having a fixed position on said garment and configured to provide at least one of:
      a) produce; and
      b) receive ultrasound signals that pass through the living body;
   iii. an ultrasound processing unit operatively associated with said at least one ultrasound transducer and configured to process said ultrasound signals following passage through the living body; and
   iv. an ultrasound operator-interface unit operatively associated with said ultrasound processing unit and configured to provide information with respect to said ultrasound signals following passage through the living body, wherein said at least one transducer comprises at least one transducer array;

including at least one electromagnetic radiation source, said at least one electromagnetic radiation source occupying at least one position of:
  i. on said garment; and
  ii. at a distance from said garment, and
said at least one electromagnetic radiation source includes at least one of:
  a. light source; and
  b. radio-frequency (RF) source,
wherein said ultrasound processing unit includes a software module configured to extract from ultrasonic reflections information regarding at least one of:
  i. local optical absorption; and
  ii. local RF absorption.

19. The assembly according to claim 18, wherein said ultrasound processing unit includes a software module-based process configured to perform at least one of the following techniques:
  i. ultrasound computed tomography;
  ii. ultrasound computed tomography with geometric transformation;
  iii. attenuation correction using local attenuation coefficient measurements; and
  iv. time-delay correction using local speed of sound measurements.

* * * * *